US012484941B2

(12) United States Patent
Jordan et al.

(10) Patent No.: US 12,484,941 B2
(45) Date of Patent: Dec. 2, 2025

(54) FLEXIBLE IMPLANT FOR FIXATING A DISJOINED PUBIC SYMPHYSIS

(71) Applicant: Julius-Maximilians-Universität Würzburg, Würzburg (DE)

(72) Inventors: Martin Jordan, Würzburg (DE); Christian Fischer, Würzburg (DE); Rainer Meffert, Würzburg (DE)

(73) Assignee: JULIUS-MAXIMILIANS-UNIVERSITÄT WÜRZBURG, Würzburg (DE)

( * ) Notice: Subject to any disclaimer, the term of this patent is extended or adjusted under 35 U.S.C. 154(b) by 163 days.

(21) Appl. No.: 18/548,407

(22) PCT Filed: Mar. 17, 2022

(86) PCT No.: PCT/EP2022/057032
§ 371 (c)(1),
(2) Date: Aug. 30, 2023

(87) PCT Pub. No.: WO2022/207348
PCT Pub. Date: Oct. 6, 2022

(65) Prior Publication Data

US 2024/0138890 A1 May 2, 2024

(30) Foreign Application Priority Data

Apr. 1, 2021 (EP) .................................... 21166707

(51) Int. Cl.
*A61B 17/80* (2006.01)

(52) U.S. Cl.
CPC ...... *A61B 17/8066* (2013.01); *A61B 17/8019* (2013.01)

(58) Field of Classification Search
CPC .. A61B 17/8066; A61B 17/8019; A61B 17/82
See application file for complete search history.

(56) References Cited

U.S. PATENT DOCUMENTS

| | | | |
|---|---|---|---|
| 10,835,301 B1 | 11/2020 | Paranjpe et al. | |
| 2007/0293863 A1 | 12/2007 | Reimels et al. | |

(Continued)

FOREIGN PATENT DOCUMENTS

| | | | |
|---|---|---|---|
| RU | 2401078 C1 | 10/2010 | |
| WO | 3047423 A2 | 6/2003 | |
| WO | 2020070596 A1 | 4/2020 | |

OTHER PUBLICATIONS

Park, et al., "Is There a Clinical Benefit of Additional Tension Band Wiring in Plate Fixation of the Symphysis?", BMC Musculoskeletal Disorders, BioMed Central, Jan. 25, 2017, 18:40, pp. 1-6.

(Continued)

*Primary Examiner* — Olivia C Chang
(74) *Attorney, Agent, or Firm* — Grossman, Tucker, Perreault & Pfleger, PLLC

(57) ABSTRACT

An implant device, in particular to a pubic symphysis implant device, and to an implant system comprising two such implant devices. The implant device of the invention comprises a bent body comprising a curved middle portion and two lateral arms extending away from the middle portion and being mutually joined by the middle portion, and at least one guiding element defining at least one guiding path along which a tensioning element can be guided. A method of fixating together a first bone or bone part and a second bone or bone part, for example for re-joining a disjoined pubic symphysis, using such an implant system, in particular by placing each of the two implant devices on corresponding bones or bone parts and by pulling the two implant devices towards each other by tensioning a tensioning element guided along the at least one guiding path of each of the two implant devices.

20 Claims, 14 Drawing Sheets

(56) References Cited

U.S. PATENT DOCUMENTS

| | | | | |
|---|---|---|---|---|
| 2015/0196331 | A1* | 7/2015 | Gordon ............. | A61B 17/7067 606/248 |
| 2015/0209093 | A1 | 7/2015 | Dallis | |
| 2018/0289496 | A1 | 10/2018 | Zappacosta et al. | |

OTHER PUBLICATIONS

Varga, et al., "Effects of Method of Internal Fixation of Symphyseal Disruptions on Stability of the Pelvic Ring", Injury: International Journal of the Care of the Injured, vol. 26, No. 2, 1995, Elsevier Science Ltd., Great Britain, pp. 75-80.

International Search Report and Written Opinion from corresponding PCT Appln. No. PCT/EP2022/057032, dated Jun. 29, 2022.

* cited by examiner

FLEXIBLE IMPLANT FOR FIXATING A DISJOINED PUBIC SYMPHYSIS

FIELD OF THE INVENTION

The present invention is in the field of implant devices and refers to an implant device, in particular to a pubic symphysis implant device, as well as to an implant system comprising two such implant devices and to a method of re-joining a disjoined pubic symphysis using such an implant system.

BACKGROUND OF THE INVENTION

The human pelvis has a ring-like structure around the pelvic cavity formed by the so-called anterior and posterior pelvic ring. The left and right hemipelvises, which are respectively formed by the ilium, the pubis and the ischium, extend around the pelvic cavity and are mutually joined posteriorly by the sacrum and the coccyx and anteriorly by the pubic symphysis (symphysis pubis). The pubic symphysis is a fibrocartilaginous junction (Amphiarthrosis) between the left and right hemipelvises at the anterior pelvic ring.

In normal adults, the pubic symphysis is slightly movable and can be minimally displaced by about 2 mm and rotated by about 10. However, when exposed to great forces or impacts, for example in a road traffic or horse ride accident or in case of falls from height, the pubic symphysis can rupture and open up leading to separation of the left and right hemipelvises (pubic symphysis diastasis, PSD). Cases of pubic symphysis can also occur in women in the course of childbirth. FIG. 1 shows an illustration of a human male pelvis with a disjoined pubic symphysis, wherein the location of the pubic symphysis is indicated by an arrow.

The separation of the left and right hemipelvises caused by a disjoined pubic symphysis leads to an instability of the frontal part of the pelvis with common symptoms including symphyseal pain aggravated by weight bearing and walking, pubic tenderness, and a noticeable interpubic gap, and usually requires surgical intervention to repair the disjoined pubic symphysis and re-join the left and right hemipelvises. Known surgical solutions are typically based on the use of an implant plate and of screws for fixating the plate to both hemipelvises. FIG. 2 shows an anatomical model of such an implant plate fixated to the left and right hemipelvises by means of screws in order to repair a disjoined pubic symphysis. FIG. 3 shows an example X-ray image of a patient implanted with such an implant plate, which is indicated by an arrow.

The implantation of such implant plates is established as a standard treatment for the surgical repair of a disjoined pubic symphysis. However, it has several possible complications including progressive or sudden loosening of the fixating screws or breakage of the plate itself, which can make a revision surgery necessary.

Therefore, there is room for technical improvement in the field of implant devices for re-joining a disjoined pubic symphysis treat PSD.

SUMMARY OF THE INVENTION

The present invention aims at providing a novel type of implant device which may be used for re-joining a disjoined pubic symphysis so as to heal PSD overcoming the aforementioned disadvantages of the known prior art, in particular in terms of possible post-operatory complications due to mechanical malfunctioning of the implanted device.

The implant device of the invention, which may in particular be a pelvis implant device, more particularly a pubic symphysis implant device, comprises a bent body comprising a curved middle portion and two lateral arms. The two lateral arms extend away from the middle portion and are mutually joined by the middle portion.

The two lateral arms may be substantially parallel to each other. “Substantially parallel” refers herein to the fact that the two lateral arms need not be strictly parallel to each other and may for example be closer separated from each other closer to the middle portion while being further away from each other further away from the middle portion. In other words, the two lateral arms may define an angle with respect to each other, which may for example be between 5° and 45°, preferably between 10° and 40°. The angle between the lateral arms may vary along the length of the lateral arms.

The bent body, which can in particular be a substantially U-shaped, C-shaped or V-shaped body, defines an open end between the two lateral arms opposite a closed end that is defined by the middle portion. Thus, the bent body can extend around and partially enclose a ground object, in particular a bone, such that the bone is surrounded by the middle portion and the lateral arms of the bent body and remains exposed by the open end of the bent body. In such a situation, an interior surface of the bent body may be facing the ground object that is surrounded by the bent body, while an exterior surface of the bent body may be facing away from the ground object.

“Interior surface” of the bent body may refer herein to a surface of the bent body on an interior side thereof, wherein a portion of the interior surface corresponding to one of the lateral arms faces a portion of the interior surface corresponding to the other one of the lateral arms. “Exterior surface” of the bent body may refer herein to a surface of the bent body on an exterior side thereof, wherein a portion of the exterior surface corresponding to one of the lateral arms faces away from a portion of the exterior surface corresponding to the other one of the lateral arms.

The middle portion extends between the two lateral arms and may materially connect the two lateral arms. However, the middle portion needs not be strictly closed or uninterrupted in geometrical terms at the closed end and may for example comprise openings or interruptions.

The implant device of the invention may further comprise at least one guiding element defining at least one guiding path extending along at least a portion of the bent body. The at least one guiding path may in particular refer to a path or trajectory followed by a tensioning element, which needs not be a component of the implant device of the invention, for example a cable, a thread or a band, when the tensioning element is arranged on the bent body, is guided along the at least one guiding path in a manner determined by the at least one guiding element, and is tensioned by tensioning forces, in particular by tensioning forces directed from the closed end of the bent body towards the open end of the bent body.

The at least one guiding path may preferably be a curved path. Each of the at least one guiding path comprises a path vertex and two path portions. “Vertex” may refer herein in general to the part of a curve having a curvature with vanishing first derivative, i.e. to a local extreme point of curvature of the corresponding guiding path. The two corresponding path portions extend away from the path vertex and further extend away from the closed end of the bent body, in particular irrespectively of where in the bent body the path vertex may be located. Thus, when a tensioning element such as a tensioning cable is guided along a guiding path, the tensioning element may follow a curved trajectory along the curved guiding path forming a vertex or point of maximum curvature of the tensioning element at a position corresponding to the path vertex and extending from said vertex on one and the other side of the path vertex with respective segments of the tensioning element extending along one and the other corresponding path portions.

As will be described below in more detail with reference to some specific embodiments, "guiding element" may be understood herein to refer to any element, which may in particular be any structural feature of the bent body, suitable for determining a path or a trajectory of a tensioning element, in particular of a string-like or cable-like tensioning element, along said at least a portion of the bent body, when the tensioning element is arranged on the bent body.

A single guiding element may be sufficient for defining a guiding path with a corresponding guiding vertex. For example, a guiding element may be formed as a guiding pin protruding from an exterior surface of the bent body (the previously described exterior surface of the bent body), such that a tensioning element, for example a tensioning cable, can be arranged on the bent body and wrapped around the guiding pin, thereby forming a vertex of the tensioning element that rests against the guiding pin and two segments of the tensioning element that extend on one side and the other of said vertex, i.e. following the path portions defined by the guiding pin.

However, alternatively a guiding path may be defined by a plurality of guiding elements. For example, a plurality of guiding elements may be arranged on an exterior surface (the previously described exterior surface of the bent body) of the bent body at different positions, such that a tensioning element, for example a tensioning cable, can be arranged on the bent body following the guiding path(s) defined by the plurality of guiding elements. For example, the guiding elements may be formed as guiding eyelets configured for passing a tensioning element therethrough. Notably, the at least one guiding path need not be continuous and may be piecewise formed on/in the bent body.

The implant device of the invention has a geometry that makes it suitable for being used as part of an implant system, in particular as part of an implant system for re-joining a disjoined pubic symphysis. Due to its geometry, the implant device, in particular the bent body thereof, is suitable for being arranged around a bone or bone part, such that the bone or bone part abuts against the interior surface of the bent body at its middle portion and such that each of the two lateral arms extend on one respective side of said bone or bone part, possibly also abutting against the bone or bone part. The implant device of the invention may be fixated to the bone or bone part to receive the implant by form fitting, in particular by dimensioning the implant device such that the shape and dimensions thereof are such that the implant device can be tightly fitted to the corresponding bone or bone part. Said bone or bone part may be the os pubis of the pelvis, wherein the implant device of the invention may in particular be attached to the medial part of the obturator foramen.

Additionally or alternatively, the implant device of the invention can be fixated to the bone or bone part to receive the implant in cooperation with a further implant device by using a "partner" implant device, which can in particular be a further implant device according to the invention, to which the implant device can be fixated using a tensioning element. As will be explained in more detail below, the implant device of the invention may in particular cooperate with another implant device according to the invention, forming a pair of implant devices. The other implant device can be arranged around the same bone or bone part or around another near bone or bone part in a similar manner. A tensioning element such as a fixation cable or a zip tie can be guided by the guiding elements of the two implant devices following the corresponding guiding paths and can be used for fixating a relative position of both implant devices and/or for pulling both implant devices towards each other, such that the implant devices can be used for holding a relative position of the bone(s) or bone parts to which they are fixated, by exerting a complementary pair of fixation forces, in particular an antagonistic pair of fixation forces.

For example, two implant devices according to the invention may be used for re-joining a disjoined pubic symphysis. A first implant device according to the invention may be placed around the (left or right) hemipelvis (os pubis) of a patient, in particular at the medial border of the respective obturator foramen, possibly fixated thereto by form-fitting, and a second implant device according to the invention may then be placed around the (right or left) hemipelvis (os pubis) of the patient, in particular at the medial border of the respective obturator foramen, possibly fixated thereto by form-fitting, such that the closed ends of both implant devices face substantially away from each other and the open ends of both implant devices substantially face towards each other (although the implant devices need not be mutually aligned). A tensioning element, in particular a flexible tensioning element such as a fixation cable, can be guided along the guiding paths defined by the guiding elements of both implant devices can then be used for pulling both implant devices towards each other, fixating both implant devices in position such that the implant devices pull both hemipelvises together and cause the pubic symphysis to re-join and to stay re-joined.

Advantageously, the implant device of the invention allows using such a tensioning element for fixating the implant device, possibly to a "partner" implant device and/or to a further implant device according to the invention, without the risk of the tensioning element damaging the implanted bone or bone part or surrounding tissue and of consequent loosening of the implant device. As the present inventors found out, if a tensioning element is used as a cerclage without one or more implant devices according to the invention, the tensioning element, in particular a vertex thereof, can cut into the bone or bone part or into surrounding tissue. According to the invention, since the tensioning element, in particular a vertex thereof, can be guided along the guiding path(s) defined by the at least one guiding element of the implant device of the invention, the tension applied by the tensioning element is spatially distributed by the implant device and the tensioning element can be prevented from cutting into the bone or bone part or into surrounding tissue. Instead, the tension can be received by the implant device and appropriately transmitted to the implanted bone or bone part at a reduced local mechanical pressure via the implant device, whereby the implant device can be securely and durably fixated.

Thus, the implant of the invention is, despite its constructional and structural simplicity, advantageously suitable for being employed as part of an implant system, in particular for re-joining a disjoined pubic symphysis in humans or in other animals, in a manner that is not known in the prior art and which offers the technical advantages that will be explained in more detail below.

The bent body may be a substantially planar stripe extending between a first longitudinal end and a second longitudinal end, wherein the first and second longitudinal ends may be arranged at the open end of the bent body. Notably, since the bent body is bent and has a curved middle portion, the "longitudinal direction" reaching from one longitudinal end, at one of the lateral arms, to the other longitudinal end, at the other lateral arm, is not a straight direction as considered in an xyz Cartesian coordinate system. The longitudinal direction may refer herein to a curved direction on the surface of the bent body pointing from one longitudinal end to the other longitudinal end, e.g. along the extension of the U-shape or C-shape.

The bent body may hence have a "length" along the longitudinal direction, i.e. a distance between both longitudinal ends in the longitudinal direction. The length of the bent body may be 50 mm to 100 mm, preferably 60 mm to 80 mm. The bent body may have a constant length throughout its transverse extension in a transverse direction perpendicular to the longitudinal direction. However, in some embodiments the bent body may have a variable length over its transverse extension, in which case the aforementioned length ranges may refer to a maximal length of the bent body. For example, a length of the bent body along the longitudinal direction at one transverse edge of the bent body may differ from a length of the bent body along the longitudinal direction at another transverse edge of the bent body.

The bent body may have a "width", in particular in a transverse direction on the surface of the bent body perpendicular to the longitudinal direction, of 5 mm to 30 mm, preferably of 10 mm to 20 mm. Such "width" may also be referred to as a "height". The bent body may have a constant width throughout its longitudinal extension. However, in some embodiments the bent body may have a variable width over its longitudinal extension, in which case the aforementioned width ranges may refer to a maximal width of the bent body.

"Substantially planar" may refer herein to the fact that the bent body may have a thickness in a third direction perpendicular to the longitudinal direction and to the transverse direction that is considerably smaller than the length and the width, but may nonetheless be non-vanishing, such that the bent body needs not be strictly planar. The bent body may have a thickness of 0.4 mm to 10 mm, preferably of 1 mm to 8 mm, more preferably of 3 mm to 6 mm.

The bent body may have a constant thickness throughout its longitudinal extension. However, in some embodiments the bent body may have a variable thickness over its longitudinal extension, in which case the aforementioned thickness ranges may refer to a maximal thickness of the bent body.

Notably, since the bent body may have a variable length over its transverse extension and/or a variable width over its longitudinal extension, the fact that the bent body may be substantially planar does not necessarily imply that the longitudinal extension of the bent body must be straight or that the bent body would extend straight—without any curvature (i.e. being I-shaped)— if it were to be unfolded such as to arrange the two lateral arms coplanar with each other. Instead, if the bent body were to be unfolded such as to arrange the two lateral arms coplanar with each other, the bent body could define a curved profile, i.e. have a curved 2-dimensional layout.

Since the longitudinal direction of the bent body is curved, the length of the bent body may not be fully indicative of a (shortest or straight) separation distance from the middle portion, in particular from an exterior surface thereof, to the open end of the bent body. Such separation distance may be 15 mm to 45 mm, preferably 25 mm to 35 mm.

A maximal distance between the exterior surfaces of the two lateral arms, for example at the open end of the bent body, may be 20 mm to 40 mm, preferably 25 mm to 30 mm. This distance may determine a maximal extension of the bent body in a direction perpendicular to the aforementioned separation between the middle portion, in particular from an exterior surface thereof, and the open end of the bent body.

In other words, an implant device according to the invention may fit in a rectangular box having a length of at least 15 mm to 45 mm, preferably of at least 25 mm to 35 mm, a width of at least 20 mm to 40 mm, preferably of at least 25 mm to 30 mm and a height of at least 5 mm to 30 mm, preferably of at least of 10 mm to 20 mm.

The implant device of the invention may have an axis of mirror symmetry bisecting the middle portion at its point of maximum curvature perpendicularly, such that the two lateral arms may be mirror symmetric with respect to each other and to such axis of mirror symmetry. Thus, the two lateral arms may have the same extension, i.e. may extend equally far away from the middle portion and/or from the closed end of the bent body. However, this needs not be the case and the implant device may also be asymmetric, such that the two lateral arms may in particular have different extensions and/or extend differently far away from the middle portion and from the closed end of the bent body. In such asymmetric configurations, the aforementioned separation distance from the middle portion to the open end may correspond to a separation distance between the middle portion, in particular an exterior surface thereof, and an extremal position located at the open end in front of the close end and aligned with the longitudinal end of the longer lateral arm of the bent body.

A maximal separation distance between the two lateral arms of the implant device, which may in particular be a separation distance between the two lateral arms at the open end, may be 10 mm to 30 mm, preferably 15 mm to 25 mm. These dimensions are suitable for the implant device of the invention to surround a bone or bone part to receive the implant, in particular the corpus of the pubis of a human pelvis. In embodiments in which the two lateral arms are substantially parallel to each other, the bent body may correspondingly be a substantially U-shaped or C-shaped body. However, in embodiments in which a separation distance between the two lateral arms varies along the length of the lateral arms, in particular increases from the closed end towards the open end, the bent body may be a substantially V-shaped body.

The two lateral arms may extend strictly parallel to each other, such that a separation distance between the two lateral arms may be constant (substantially U-shaped/C-shaped bent body). However, this needs not be the case and in some preferred embodiments, a separation distance between the two lateral arms may increase from the closed end towards the open end of the bent body, possibly monotonously and/or continuously. Thus, the two lateral arms may progressively space apart from the closed end, at which their mutual separation distance may be minimal, towards the open end, at which their mutual separation distance may be maximal. The bent body may then substantially have a smooth V-shape, in particular with no abrupt discontinuity in the longitudinal direction, i.e. no cusp. Such configurations in which the separation distance between the two lateral arms may increase from the closed end towards the open end of the bent body may allow an anatomically adapted fit of the implant device to a bone with a corresponding or pointed form, in particular to the corpus of the pubic bone.

By being dimensioned and shaped according to the previously described numerical ranges and configurations, the implant device of the invention can fit the dimensions of a human bone or bone part, in particular of the human pelvic bone, which allows the implant device of the invention to be tightly fitted thereto. As the skilled person shall understand, it is possible to design and manufacture an implant device according to the invention having shape and dimensions specifically adapted to the shape and dimensions of the target bone or bone part to receive the implant device, for example, by additive manufacturing based on 3D image data (e.g. computer tomographic data) acquired from a corresponding patient before or during intervention/surgery.

According to some embodiments, the bent body may further comprise one or more through-openings connecting and/or communicating an exterior surface of the bent body (the previously described exterior surface of the bent body) with an interior surface thereof (the previously described interior surface of the bent body). The one or more through-openings may allow fixating or attaching the implant device to a ground object, in particular to a bone or bone part, by receiving a fixation element such as a fixation screw or a fixation bolt through the one or more through-openings. For example, a fixation screw received in one of the one or more through-openings may fixate the implant device of the invention to a bone or bone part by being fixedly attached, in particular screwed, to the bone or bone part. This ensures that the relative position of the implant device with respect to the ground object can be held in place. Said bone or bone part may in particular be the os pubis of the pelvis.

These embodiments allow additional fixation of the implant device to the bone or bone part to receive the implant. For example, as previously explained, two implant devices according to the invention may be used for re-joining a disjoined pubic symphysis. A first implant device according to the invention may be placed around the corpus of the left or right hemipelvis (os pubis, medial border of the obturator foramen) of a patient and fixated thereto using a first fixation element such as a fixation screw or a fixation bolt passing through one or two of the one or more through-openings thereof and through the same (left or right) hemipelvis. A second implant device according to the invention may then be placed around the corpus of the right or left hemipelvis (os pubis, medial border of the obturator foramen) of the patient and fixated thereto using a second fixation element such as a fixation screw or a fixation bolt passing through one or two of the one or more through-openings thereof and through the (right or left) hemipelvis, such that the closed ends of both implant devices face away from each other (and the open ends of both implant devices face towards each other). A tensioning element, in particular a flexible tensioning element such as a fixation cable, can be guided along the guiding paths defined by the guiding elements of both implant devices can then be used for pulling both implant devices towards each other, such that the implant devices pull both hemipelvises together and cause the pubic symphysis to re-join and to stay re-joined.

In some embodiments, the one or more through-openings may be formed in one or both of the lateral arms. In some embodiments, at least one of the one or more through-openings, in particular one of them, may be formed in one of the lateral arms, preferably proximal to the open end of the bent body, and at least another one of the one or more through-openings, in particular another one of them, may be formed in the other lateral arm, preferably proximal to the open end of the bent body. The at least one through-opening in one of the lateral arms may then be aligned with the at least one through-opening in the other one of the lateral arms.

The through-openings on each of the lateral arms may be arranged proximal to the open end of the bent body, i.e. closer to the open end of the bent body than to the closed end thereof. Since the open end of the bent body is defined by the longitudinal ends of the lateral arms, this may in particular imply that the through-openings may be formed in a vicinity of the longitudinal ends of the lateral arms, which form the open end of the bent body. Referring to a U-shape (or C-shape) or a V-shape of the bent body, the through-openings may hence be formed in the upper portion of the lateral arms of the "U", "C" or "V" correspondingly. This position is an optimal position for fixating the implant device of the invention to a bone or bone part using a fixation element, for example a fixation screw, passed through the corresponding through-openings. Such fixation element can be anchored on one side or on both sides of the cortical bone.

For example, the implant device may comprise two through-openings, each being formed in one of the mutually opposed lateral arms and arranged in front of each other, i.e. aligned with each other, such that it may be possible to draw an imaginary straight-line crossing both through-openings, wherein such imaginary straight-line may be substantially perpendicular to the surfaces of the bent body at the respective longitudinal ends of the lateral arms. Both through-openings may be formed at (proximal to) the open end of the bent body, i.e. at a respective longitudinal end of the bent body. This way, the implant device can be placed on a bone or bone part such that a fixation element received through the two through-openings and used to fixate the implant device to the bone or bone part can be arranged across a greater portion of bone, thereby providing better fixation. The same applies to embodiments in which only one through-opening may be formed in one of the lateral arms, at the respective open end of the bent body.

According to some embodiments, the through-openings may be configured for receiving a fixation element therethrough, in particular a fixation screw, such that the fixation element joins the two lateral arms. Since the through-openings of the two lateral arms may be aligned with each other, it may be possible to pass the same fixation element through both through-openings. This allows fixating the implant device of the invention to a bone or bone part by passing the fixation element through the first one of the through-openings, then through the bone, and then through the other one of the through-openings, wherein to reduce invasiveness, the first one of the through-openings may preferably correspond to a side of the body of a recipient of the implant device on which an incision is made by a surgeon for the surgical intervention, for example to a ventral side of the pelvis of the recipient of the implant device.

Preferably, one or more of the through-openings may be threaded openings, i.e. may have an inner threaded profile. If one or more of the through-openings is threaded, a fixation screw can advantageously be screwed through said one or more of the through-openings. This allows using a fixation screw for fixating the implant device to a bone or bone part and, at the same time, fixating a relative position, in particular a relative angle, of the fixation screw with respect to the implant device, thereby improving the stability and durability of the implant. Further, the use of at least one threaded through-opening, which may in particular be arranged in a lateral arm of the implant device ventrally accessible from the exterior of the body of a patient receiving the implant, may allow fixating a threaded drill bushing to the threaded through-opening such as to orient and guide a drilling tool used during surgery for drilling through the bone or bone part embraced by the implant device to drill a drill-hole through which a fixation element such as a fixation screw can be introduced for fixating the implant device to the bone or bone part being received in at least one, possibly two, through-openings of the implant device.

According to some embodiments, one through-opening may be formed in one of the lateral arms and a partial opening may be formed on the inner surface of the bent body in the other lateral arm aligned with the through-opening formed in said one of the lateral arms. A partial opening refers herein to an opening formed on one surface of the bent body, in particular on the interior surface thereof, without reaching through the bent body all the way to the exterior surface of the bent body. In other words, while a through-opening extends through the bent body completely, a partial opening has a depth that is less than the thickness of the bent body. Thus, a fixation element such as a fixation screw or a fixation bolt may be received through the through-opening in one of the lateral arms, crossing said one of the lateral arms, may extend across the space separating the two lateral arms, in particular through a corresponding bone or bone part, and may then be received within the partial opening formed in the other one of the lateral arms, which can then act as a stopper preventing that the fixation element can uncontrolledly penetrate through the other lateral arm completely, possibly damaging tissues located behind the other lateral arm. The aforesaid partial opening may preferably be a threaded partial opening, such that a fixation screw can be screwed thereto.

Additionally or alternatively, a fixation screw passed through the through-openings of the implant device of the invention may be fastened to the implant device (and to a bone) using a suitable nut.

According to some embodiments, at least one of the one or more through-openings may have a substantially circular shape and/or may have a diameter of 1 mm is to 10 mm, preferably 3 mm to 6 mm. By having such geometry, the through-openings may be suitable for tightly receiving therein a screw or another fixation element having a corresponding (nominal) diameter of 1 mm is to 10 mm, preferably of 3 mm to 6 mm, which may offer an optimal balance between mechanical stability fixation and surgical invasiveness. In the case of a non-circular through-opening, "diameter" may refer to an aperture size of the corresponding opening, i.e. to an opening width or length.

According to some embodiments, at least one of the one or more through-openings may be a stepped opening having a first diameter proximal to the exterior surface of the bent body and a second diameter proximal to the interior surface of the bent body, wherein the second diameter may be smaller than the first diameter. Said at least one of the one or more through-openings may hence comprise a shoulder at a position along the thickness of the bent body arranged between the exterior surface and the interior surface, which shoulder implements a transition from the first diameter to the second diameter. The stepped profile of the through-openings may be suitable for receiving a screw having a diameter corresponding to the second diameter and a corresponding fastening nut having an exterior diameter smaller than or equal to the first diameter and/or for receiving a screw having a diameter corresponding to the second diameter and a screw head having a spanner size (i.e. a head width) smaller than or equal to the first diameter. The shoulder or step formed at the transition between the first diameter and the second diameter may act as a stopper for the screw head or for the nut. The first diameter may be 2 mm to 12 mm, preferably a 4 mm to 9 mm. The second diameter may be 1 mm to 10 mm, preferably 3 mm to 6 mm.

It is also possible within the context of the present invention for an implant device to comprise the aforementioned one or more through-openings and no guiding element/guiding path. However, in preferred embodiments, the implant device may comprise the previously described at least one guiding element, optionally combined with the aforementioned one or more through-openings.

As previously mentioned, different configurations are foreseen within the context of the present invention for the guiding elements and the guiding paths they define.

According to some embodiments, one or more of the at least one guiding element may be formed at least in part protruding from and/or recessing into an exterior surface of the bent body (the previously described exterior surface of the bent body). Each of said at least one guiding element may hence be formed as a protrusion and/or a recess on the exterior surface of the bent body that can be used for determining the corresponding guiding path. Each of said at least one guiding element may also be formed as a part of a protrusion and/or as part of a recess formed by more than one of the at least one guiding elements on the exterior surface of the bent body. One same guiding element can possibly be formed in part protruding from the exterior surface and in part recessing into the exterior surface. By protruding from the exterior surface of the bent body and/or by recessing into the exterior surface of the bent body, said guiding element can restrict a mobility of a tensioning element arranged on the bent body and guided along the at least one guiding path, in particular a mobility of the tensioning element in a transverse direction.

According to some embodiments, one or more of the at least one guiding element may form a support surface, wherein the support surface may have at least a perpendicular component with respect to an exterior surface of the bent body. This means that a relative angle between the support surface and the exterior surface of the bent body may be greater than 0° and less than or equal to 90°, i.e. may have at least a component in a direction perpendicular to the exterior surface of the bent body. In other words, the support surface may be completely or partly perpendicular to the exterior surface of the bent body. This allows the support surface, which may in particular protrude from the exterior surface of the bent body and/or recess into the exterior surface of the bent body, to act as a support structure that can determine a guiding path of a tensioning element, and against which such tensioning element can abut when being tensioned, thereby being held in position and transmitting the tensioning force to the bent body. Additionally or alternatively, the support surface may face away from the open end of the bent body. This may allow a tensioning element transmitting to the bent body a tensioning force directed towards the open end of the bent body in an efficient manner.

For example, a guiding element may be formed as a recess in the exterior surface of the bent body and may be configured for receiving a tensioning element, for example a tensioning cable, therein, thereby determining at least a part of a guiding path followed by the tensioning element on the bent body. The tensioning element can then be held in place within the recess and, when a tensioning force is applied to the tensioning element, the tensioning element presses against a sidewall of said recess, which then acts as a support surface and transmits the tensioning force to the implant device.

One or more of the at least one guiding element may comprise or be a guiding pin and/or a guiding surface protruding from an exterior surface of the bent body (the previously described exterior surface). By protruding from the exterior surface, a guiding pin or a guiding surface may then define a corresponding support surface against which a tensioning element can abut, whereby a guiding path followed by the tensioning element is determined and whereby the tensioning element can transmit a tensioning force to the implant device.

According to some embodiments, the at least one guiding element may be or comprise at least one guiding channel extending along at least a portion of the bent body. Each of the at least one guiding channel may comprise a channel vertex and two channel portions extending away from said channel vertex and from the closed end of the bent body. Said channel vertex may correspond to a path vertex of the at least one guiding path and said channel portions may correspond to respective path portions of the at least one guiding path.

Each guiding channel may in particular define one of the at least one guiding path. Thus each of the at least one guiding channel may be configured for receiving a tensioning element therein, for example a cable, a thread or a band, and for guiding such tensioning element. The at least one guiding channel may preferably follow a curved path. Each guiding channel may comprise a corresponding channel vertex defining a path vertex and two corresponding channel portions defining respective path portions. The two channel portions may extend away from the channel vertex and may further extend away from the closed end of the bent body, in particular irrespectively of where in the bent body the channel vertex may be located. Notably, the at least one guiding channel need not be continuous and may be piecewise formed on/in the bent body.

For example, if the vertex is located at the middle portion of the bent body, the two corresponding channel portions may respectively extend on one side of the vertex and the other, along one lateral arm and the other, towards the open end of the bent body. In another example, if the vertex is located in one of the lateral arms of the bent body, the two corresponding channel portions may extend on said lateral arm from a portion of the lateral arm closer to the closed end (i.e. closer to the middle portion) to a portion of the lateral arm closer to the open end.

According to some embodiments, the at least one guiding channel may be formed at least in part as a recess on the exterior surface of the bent body. A tensioning element such as a fixation cable can then be received within the at least one guiding channel in a simple—and hence minimally invasive—manner by simply positioning the fixation cable into the at least one guiding channel on the exterior surface of the bent body. Further, this reduces the manufacturing complexity and cost of the implant device of the invention, since the at least one guiding channel may be formed in a simple manner by forming a corresponding groove on the exterior surface of the bent body during a manufacturing process of the bent body.

Such recess may have a width (in the transverse direction along the plane of the exterior surface of the bent body) of 0.5 mm to 2.5 mm, preferably of 1.5 mm to 2.0 mm and may have a depth (in a direction perpendicular to the plane of the exterior surface of the bent body) of 0.5 mm to 2.5 mm, preferably of 1.5 mm to 2.0 mm, for example of 1.9 mm. These dimensions may make the at least one guiding channel suitable for tightly receiving therein and keeping in place a fixation cable having a thickness of 1 mm to 3 mm, preferably of 1.5 mm to 2 mm, for example of 1.7 mm. For example, a guiding channel may be formed as a recess on the exterior surface of the bent body having a width and a depth of 1.9 mm and a tensioning element such as a tensioning cable having a diameter of 1.7 mm may be received therein. The tensioning element may in particular be completely received within the recess, i.e. without protruding outwardly from the exterior surface of the bent body.

Additionally or alternatively, the at least one guiding channel may be formed at least in part as a passage hole (i.e. a cannula) tunnelling through a portion of the bent body. Having at least a portion formed as such a passage hole, the at least one guiding channel can prevent a tensioning element such as a tensioning cable received in/on the guiding channel from accidentally sliding off the guiding channel, for instance due to bone motion. For example, a guiding channel may have a portion formed as a recess on the exterior surface of the bent body and a portion formed as a passage hole tunnelling through the bent body. The passage hole may have a diameter of 0.5 mm to 2.5 mm, preferably of 1.5 mm to 2.0 mm. It is also possible for the at least one guiding channel to be partially or completely formed as a laterally open passage hole, i.e. as a cannula having an open portion corresponding to an external side of the at least one guiding channel allowing a tensioning element such as a tensioning cable to be laterally inserted into the at least one guiding channel.

For example, the at least one guiding channel may comprise two guiding channels and two through-openings formed in the bent body in respective lateral arms, wherein a first one of the two guiding channels may be formed in one of the lateral arms partly surrounding the through-opening formed therein and a second one of the two guiding channels may be formed in the other one of the lateral arms partly surrounding the through-opening formed therein.

According to some embodiments, one or more of the at least one guiding element may be formed by and/or may comprise a concavity of an exterior surface of the bent body (the previously described exterior surface) in the transverse direction, preferably at least in the middle portion. Although the exterior surface may be at least in part convex when considered along the longitudinal direction, it may be at least in part concave when considered in the transverse direction, meaning that the transverse edges of the exterior surface of the bent body may protrude outwardly from an intermediate section of the exterior surface of the bent body arranged between said transverse edges. In other words, the exterior surface of the bent body may form a so-called saddle surface being convex in the longitudinal direction and being concave in the transverse direction. The concavity or valley defined by the exterior surface may then define at least a part of a corresponding guiding path. When a tensioning element arranged on the bent body is tensioned, the tensioning element positions itself following at the bottom of the concavity or valley defined by the exterior surface. The geometry of the bent body may hence act as a guiding element and may define at least a part of a corresponding guiding path. Additionally or alternatively, one or more of the at least one guiding element may comprise a protruding lip formed at one transverse edge of the bent body.

In some preferred embodiments, the at least one guiding element may be configured such that the path vertex of one or more of the at least one guiding path may be formed in one of the lateral arms. Each of the path portions may extend on said lateral arm away from the corresponding path vertex towards the open end of the bent body. Preferably, the path vertex may be formed between the middle portion and a corresponding through-opening and each of the path portions may extend on said lateral arm away from the corresponding path vertex towards the open end of the bent body, possibly all the way to the open end of the bent body, on one respective side of the corresponding through-opening, such that said through-opening may be partly surrounded by the respective guiding path. The one or more of the at least one guiding path may hence be formed in one lateral arm and may be curved around a corresponding through-opening formed in that lateral arm, having both path portions pointing towards and/or extending all the way to the open end of the bent body. For example, a guiding channel defining a guiding path may be formed on one of the lateral arms curving around a through-opening, such that the through-opening may have the channel vertex of the guiding channel to its left, the open end of the corresponding lateral arm to its right, one of the channel portions of the guiding channel before it and the other one of the channel portions of the guiding channel behind it.

In some preferred embodiments, the at least one guiding element may be configured such that the path vertex of one or more of the at least one guiding path may be formed in the middle portion of the bent body and each of the corresponding path portions may extend on a respective one of the lateral arms away from the middle portion towards the open end of the bent body. Preferably, the at least one guiding path may be formed proximal to a transverse edge of the bent body, i.e. at one end of the bent body in the transverse direction, wherein the opposed transverse ends of the bent body may be separated by a distance approximately corresponding to a width of the bent body or corresponding to 40% to 90% of the width of the bent body. The bent body extends in a direction perpendicular to the longitudinal direction and parallel to its exterior surface from one transverse edge to the other (opposite) transverse edge.

The at least one guiding element may in particular be configured such that a first guiding path may be formed proximal to one transverse edge of the bent body and/or a second guiding path may be formed proximal to the other transverse edge of the bent body. The second guiding path may hence be separated from the first guiding path by a distance corresponding to approximately the width of the bent body or corresponding to 40% to 90% of the width of the bent body. "Proximal to a transverse end" may in particular mean that a separation distance in the transverse direction between the corresponding guiding element and the corresponding transverse end of the bent body may correspond to 30% or less, preferably 15% or less of the width of the bent body. Both the first guiding path and the second guiding path may extend, substantially parallel to each other, from one longitudinal end of the bent body to the other longitudinal end of the bent body, having a corresponding vertex in the middle portion of the bent body. Embodiments having such configuration of two parallel guiding paths allow using a tensioning element such as a tensioning cable passed twice around the implant device being guided through the respective (first and second) guiding paths or using two tensioning elements each passed once around the implant device being guided through the respective (first or second) guiding path. In both cases, the stability and durability of an implant system including the implant device can be improved as compared to embodiments using a single tensioning element passed once around the implant device, in particular with respect to the resistance to shearing forces. For example, one guiding element may be formed as a first guiding channel formed at one transverse edge of the bent body, in particular at a distance of 2 mm from said one transverse edge of the bent body, and another guiding element may be formed as a second guiding channel formed at the other transverse edge of the bent body, in particular at a distance of 2 mm from said other transverse edge of the bent body, which is separated from the firstly mentioned transverse edge by a distance corresponding to the width of the bent body. Both the first guiding channel and the second guiding channel may extend from one longitudinal end of the bent body to the other longitudinal end of the bent body, having a corresponding vertex in the middle portion of the bent body. One tensioning element such as a tensioning cable may be passed twice around the implant device being received within the respective (first and second) guiding channels or, alternatively, two tensioning elements may be each passed once around the implant device being each received within a respective (first or second) guiding channel.

In some embodiments, the middle portion of the bent body may be tilted at the closed end with respect to a transverse direction of each of the lateral arms extending between opposing transverse edges of the bent body, such that a separation distance between the middle portion and the open end may increase, possibly continuously and/or monotonously, along the middle portion in the transverse direction. In other words, a separation distance between the middle portion and the open end may be smaller at one transverse edge than at the other transverse edge. Such tilted form of the middle portion may allow better fitting the implant device to a bone or bone part to receive the implant, in particular to the corpus of the pelvis of the hemipelvis of a human implant recipient.

The bent body, comprising the middle portion and the two lateral arms, may be a one-piece body. The bent body may be made of a metal or metal alloy, preferably stainless steel, titanium, a titanium alloy and/or a magnesium alloy, of a bio-absorbable material, preferably polydioxanone, or any combination thereof. The bent body may for example be made of Ti-6Al-4V or of cool formed or soft-annealed stainless steel. An implant device comprising or being made of a metal or metal alloy may have mechanical properties resembling those of bone tissue and may provide durability and mechanical stability to the implant device. An implant device comprising or being made of a bio-absorbable material may reduce invasiveness, inasmuch as the implant material can be progressively absorbed into surrounding tissue, in particular after a post-operatory time long enough for the implant device to be no longer necessary.

The bent body of the implant device of the invention may be 3D printed, molded, additively manufactured and/or CNC-machined. The possibility of 3D-printing/additively manufacturing the implant device of the invention, together with the simple geometry thereof, allows manufacturing an implant device that may be specifically tailored to a particular bone or bone part of a patient to receive the implant, i.e. a personalised implant device. For example, it may be possible to take precise measurements of the geometry of a bone or bone part to receive the implant during an operative intervention, for example using a CT scanner, and to 3D-print, possibly in situ, one or more, in particular for example two, implant devices according to the invention having a geometry and size specifically designed to fit the corresponding bone or bone part, for example a pelvic bone of the patient.

The bent body of the implant device of the invention may in particular be 3D printed using Cold-Metal-Fusion (CMF). The bent body of the implant device of the invention may be 3D printed using CMF using a metal powder, for example titanium powder, and a polymeric binder.

The invention further refers to an implant system comprising a first implant device according to any of the previously discussed embodiments and a second implant device according to any of the previously discussed embodiments and further comprising at least one tensioning element for pulling the first and second implant devices towards each other by tension by being guided along one or more of the at least one guiding path of the first implant device, in particular along one or two of them, and along one or more of the at least one guiding path of the second implant device, in particular in one or two of them.

As previously explained, such an implant system comprising a cooperating pair of implant devices according to the invention can be used to apply a fixating tension to one or more bones or bone parts by fixating the two implant devices at different positions of the one or more bones or bone parts, in particular in opposed positions with the open ends of the first and second implant devices facing each other, any by pulling the first and second implant devices towards each other by tensioning the at least one tensioning element guided along the one or more guiding paths of each of the first and second implant devices by the corresponding guiding elements.

For example, the implant system according to the invention may be used for re-joining a disjoined pubic symphysis. The first implant device of the system may be placed around the corpus of the (left or right) hemipelvis (os pubis) of a patient and fixated thereto, for example by form-fitting and/or using a screw passing through the one of the through-openings thereof and through the (left or right) hemipelvis. The second implant device of the implant system may then be placed around the (right or left) hemipelvis (os pubis) of the patient and fixated thereto, for example by form-fitting and/or using a screw passing through one of the through-openings thereof and through the (right or left) hemipelvis. The first and second implant devices may in particular be placed such that the closed ends of both implant devices substantially face away from each other and the open ends of both implant devices substantially face towards each other, i.e. such that for each implant device, one of the lateral arms extends on the respective hemipelvis ventrally and the other one of the lateral arms extends on the respective hemipelvis dorsally, i.e. with the implant device extending through the corresponding left or right obturator foramen (foramen obturatum). A tensioning element, for example a tensioning cable, may be guided through the guiding paths of both implant devices and can then be used for pulling both implant devices towards each other by being properly tensioned, such that the implant devices pull both hemipelvises together and cause the disjoined pubic symphysis to re-join and to stay in that state held by the implant system.

Notably, the first and second implant devices, when implanted, need not be aligned with each other, since for example the left and right hemipelvises are not aligned with each other but instead angled with respect to each other (as seen from above).

The at least one tensioning element may be or comprise at least one flexible tensioning element. Advantageously, the mechanical connection between the first and second implant devices is provided by the at least one flexible tensioning element, which may be or may comprise a non-rigid element, in particular a string-like and/or cable-like element having a flexible shape adaptable to take any form between two or more given points, able of transmitting a tension applied thereto. Since the at least one flexible tensioning element does then not have a strictly rigid form, unlike for example a rigid plate, the implant devices of the implant system of the invention can be slightly moved and/or rotated with respect to each other without losing their fixation effect. If the bones or bone parts to which the first and second implant devices of the implant system of the invention move with respect to each other, the at least one flexible tensioning element can flexibly adapt to the corresponding form and orientation of a bone or bone joined, for example in the case of the pubic symphysis, while still holding both implant devices to each other.

The implant system of the invention can hence allow for some rotation and motion tolerance of a pubic symphysis equipped with an implant system according to the invention without being exposed to great mechanical stresses. Consequently, the implant system of the invention is more adaptive, flexible and hence more durable as compared to more rigid implant systems known from the prior art such as implant plates. In particular, the implant system of the invention allows fixating and re-joining a disjoined pubic symphysis in a flexible and adaptive manner, better resembling and reproducing the natural properties of a cartilaginous junction and preventing the post-operative complications that are related to the use of more rigid implant systems such as implant plates, and hence providing a more durable solution.

The at least one tensioning element may be or may comprise a fixation cable, preferably a metallic cable, more preferably a steel cable or a steel band, a surgical suture and/or a surgical suture tape. This allows the implant system of the invention to perform better than the rigid implant systems known from the prior art, in particular in terms of flexibility and adaptability, while being sufficiently resistant to tensile strengths, in particular to vertical shear forces and horizontal traction forces, to which the implant system may be exposed in the post-operative period. The at least one fixation cable may have a diameter of 1 mm to 3 mm, preferably of 1.5 mm to 2 mm. Notably, the at least one fixation cable needs not be a cable with round cross-section but may instead have for example a polygonal or planar cross-section. The at least one tensioning element may be an element other than a cable, for example a zip tie, a band, a chain or the like.

Although the adaptability and flexibility that can be provided by the at least one flexible tensioning element by being non-rigid may be a significant advantage of the implant system of the invention, it is however possible, additionally or alternatively, to combine the first and second implant devices with at least one rigid tensioning element in an implant system, wherein the at least one tensioning element may for example be or comprise a rigid plate and/or a rigid rod. Each of the first and second implant devices may comprise means for fixating the at least one rigid tensioning element thereto, for example using a screw or the like. In such embodiments, the first and second implant devices need not comprise any guiding path and/or any guiding element.

According to some embodiments, the implant system may further comprise a tensioning device for closing and tensioning the at least one tensioning element for pulling the first and second implant devices towards each other. The at least one tensioning element may hence be first arranged in the corresponding guiding channels in a non-tensioned loose state, which may simplify the task of the intervening surgeon, any may thereupon be tensioned by using the tensioning device, in particular by regulating a length of a tensioned portion of the at least one tensioning element, thereby adjusting a pulling force acting upon the first and second implant devices.

The tensioning device may be or may comprise a crimping device such as cable crimp for crimping each of the at least one tensioning element at two crimping points in order to adjust a length of a tensioned portion of the at least one tensioning element. The crimping device may comprise a mechanism, for example a Ratchet mechanism, configured for allowing opposed ends of the at least one tensioning element to pass therethrough in a first configuration, such that a length of the tensioned portion of the at least one tensioning element can be adjusted, and for blocking the at least one tensioning element in order to fixate the length of the tensioned portion of thereof in a second configuration, such that the tensioned length of the at least one fixation end—and hence the pulling force acting upon the first and second implant devices—can be maintained once it has reached a desired level. The crimping device may for example be a metallic tubular structure, wherein the first configuration may correspond to an uncompressed state of the metallic tubular structure in which the corresponding tensioning element is not crimped by the metallic tubular structure, and the second configuration may correspond to a compressed state of the metallic tubular structure in which the tubular structure crimps the corresponding tensioning element.

According to some embodiments, the first and second implant devices may be substantially mirror symmetrical with respect to each other. This may allow providing a left-right pair of bones with the implant system of the invention using the first implant device for the left (or right) bone and using the second implant device for the right (or left) bone. When implanted, the first and second implant devices may then mimic the same mirror symmetry shown by the left-right pair of bones. This may in particular be the case when the implant system of the invention is used as a pubic symphysis implant, wherein the first implant device is attached to the left (or right) hemipelvis (os pubis) and the second implant device is correspondingly attached to the right (or left) hemipelvis (os pubis). After implantation, the first and second implant devices may be arranged (substantially) mirror symmetrically with respect to each other, just like the left and right hemipelvises are mirror symmetric with respect to each other. "Substantially mirror symmetrical" may in particular refer herein to the fact that the shape of the bent bodies of the first and second implant devices may be mirror symmetrical with respect to each other, but it should be taken into account that isolated features may break the mirror symmetry due to technical requirements that are apparent to a skilled person. For example, in embodiments comprising threaded through-openings, the thread direction of the through-openings in the first and second implant devices may break the mirror symmetry, for example such that a screwing direction from a ventral direction can be the same for both implant devices despite the otherwise present mirror symmetry.

The implant system of the invention may further comprise a first fixation element for fixating the first implant device to a ground material, in particular to a first bone or bone part, by being received through one of the through-openings of the first implant device, and a second fixation element for fixating the second implant device to a ground material, in particular to a second bone or bone part, by being received through one of the through-openings of the second implant device. The first and second fixation elements may be identical. Each of the first and second fixation elements may be or may comprise a screw, in particular a screw specifically configured for fitting through a corresponding one of the through-holes and for operating with the implant system of the invention, in particular in terms of dimensions.

In embodiments in which each of the first and second implant devices of the implant system comprises one through-opening formed in each of the lateral arms thereof, with both through-openings in each implant device being aligned with each other and being configured to receive a fixation element therethrough, the first fixation element may be configured for fixating the first implant device to the ground material, in particular to the first bone or bone part, by being received through both of the through-openings of the first implant device and through the ground material, in particular to the first bone or bone part, extending therebetween, and the second fixation element may be configured for fixating the second implant device to the ground material, in particular to the second bone or bone part, by being received through both of the through-openings of the second implant device and through the ground material, in particular to the second bone or bone part, extending therebetween.

The first fixation element and/or the second fixation element may be or may comprise a fixation screw, preferably a fixation screw having a nominal diameter of 1 mm to 10 mm and/or a spanner size of 2 mm to 12 mm, more preferably having a nominal diameter of 3 mm to 6 mm and/or a spanner size of 4 mm to 9 mm.

The invention further refers to a method of fixating together a first bone or bone part and a second bone or bone part, in particular for re-joining a disjoined pubic symphysis, using an implant system according to the invention. Other joints may also receive an implant system according to the invention, for example a disrupted tibiofibular syndesmosis, a disrupted mandibular symphysis or a disrupted distal radio-ulnar joint with an Essex-Lopresti fracture. The first and second bones may correspond to the left and right bone of a left-right bone pair such as the left and right hemipelvises. The first and second bone parts may however also correspond to different parts of one and the same bone, such as the sternum the mandible or a knee patella, for example a left part and a right part. The geometry and shape of the implant devices and the implant system according to the invention may be appropriately adapted to the geometry and shape of a bone or bone part to which the implant devices are to be provided.

The method of the invention comprises arranging the first implant device around the first bone or bone part, such that the first bone or bone part is partly surrounded by the bent body of the first implant device, arranging the second implant device around the second bone or bone part, such that the second bone or bone part is partly surrounded by the bent body of the second implant device, and pulling the first and second implant devices towards each other by tensioning the at least one tensioning element, wherein the at least one tensioning element is arranged along one or more of the at least one guiding path of the first implant device and along one or more of the at least one guiding path of the second implant device.

According to some embodiments, the implant device may be provided with the at least one tensioning element already arranged along the one or more of the at least one guiding path of the first implant device and along the one or more of the at least one guiding path of the second implant device. Since the at least one tensioning element is already in position guided by the guiding elements of the first implant device along the corresponding at least one guiding path of the first implant device and by the guiding elements of the second implant device along the corresponding at least one guiding path of the second implant device, the first and second implant devices can be pulled towards each other by simply tensioning the at least one tensioning element, for example by adjusting its tensioned length.

In other embodiments, the method may further comprise arranging the at least one tensioning element along the one or more of the at least one guiding path of the first implant device and along the one or more of the at least one guiding path of the second implant device. Once the at least one tensioning element is arranged along the guiding paths of the first and second implant devices, the first and second implant devices can be pulled towards each other by simply tensioning the at least one tensioning element, for example by adjusting its tensioned length.

According to some embodiments, arranging the first implant device around the first bone or bone part may comprise fixating the first implant device to the first bone or bone part, preferably using a first fixation element passing through at least one of one or more through-openings formed in the bent body of the first implant device, for example through through-openings of the first implant device formed in opposed lateral arms and through a portion of the first bone or bone part extending between both lateral arms. Arranging the second implant device around the second bone or bone part may correspondingly comprise fixating the second implant device to the second bone or bone part, preferably using a second fixation element passing through at least one of one or more through-openings formed in the bent body of the second implant device, for example through through-openings of the second implant device formed in opposed lateral arms and through a portion of the second bone or bone part extending between both lateral arms.

The at least one tensioning element may be tensioned using a tensioning device, preferably a crimping device.

According to a first variant of the method of the invention, the at least one tensioning element may extend between one lateral arm of the first implant device, preferably only one, and one lateral arm of the second implant device, preferably only one, on one side of the first bone or bone part, preferably only one, and on one (the same) side of the second bone or bone part, preferably only one. For example, a tensioning element may extend only on a frontal side of the left and right hemipelvises and hence on a frontal side only of the pubic symphysis, i.e. without crossing the obturator foramen.

According to a second variant of the method of the invention, the at least one tensioning element may extend between one lateral arm of the first implant device and one lateral arm of the second implant device and between the other lateral arm of the first implant device and the other lateral arm of the second implant device on two sides of the first bone or bone part and on the same two sides of the second bone or bone part. For example, a tensioning element may extend on both a frontal side and on a dorsal side of the left and right hemipelvises and hence on both a frontal side and a dorsal side of the pubic symphysis, i.e. crossing the obturator foramen.

DETAILED DESCRIPTION OF PREFERRED EMBODIMENTS OF THE INVENTION

Figure 1:
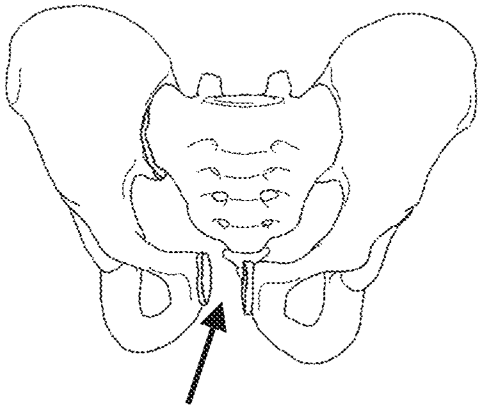
FIG. 1 shows a schematic illustration of a human pelvis with a disjoined pubic symphysis.

For the purposes of promoting an understanding of the principles of the invention, reference will now be made to specific preferred embodiments illustrated in the drawings, and specific language will be used to describe the same. It will nevertheless be understood that no limitation of the scope of the invention is thereby intended, such alterations and further modifications in the illustrated apparatus and such further applications of the principles of the invention as illustrated therein being contemplated as would normally occur now or in the future to someone skilled in the art to which the invention relates within the scope defined by the claims.

FIG. 1 shows a schematic illustration of a human pelvis with a disjoined pubic symphysis (open-book pelvic injury), which is indicated in FIG. 1 with an arrow. The pubic symphysis, at which the left and right hemipelvises (os pubis) join, is normally—in healthy subjects—a connected cartilaginous joined. In FIG. 1 the pubic symphysis is disjoined, possibly as a consequence of an accident or a strong impact.

Figure 2:
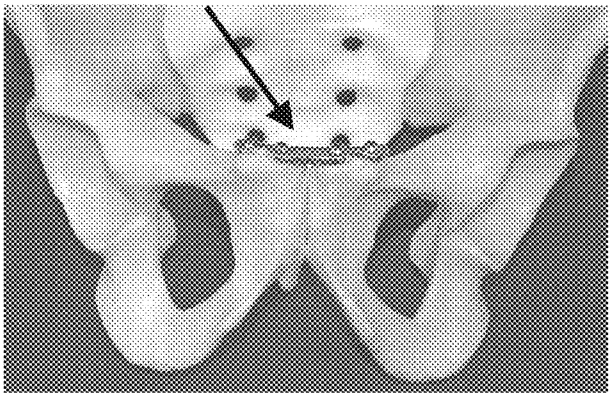
FIG. 2 shows an anatomic model of a re-joined pubic symphysis secured using a rigid implant plate known from the prior art.

FIG. 2 shows a pelvic bone model illustrating the use of a rigid 4-hole steel implant plate known from the prior art for re-joining a disjoined pubic symphysis. The implant plate rests on the upper part of the left and right pubic tubercles, and is fixated to each of the left and right superior pubic rami with a pair of screws, such that the pubic symphysis is rigidly held in a re-joined position.

Figure 3:
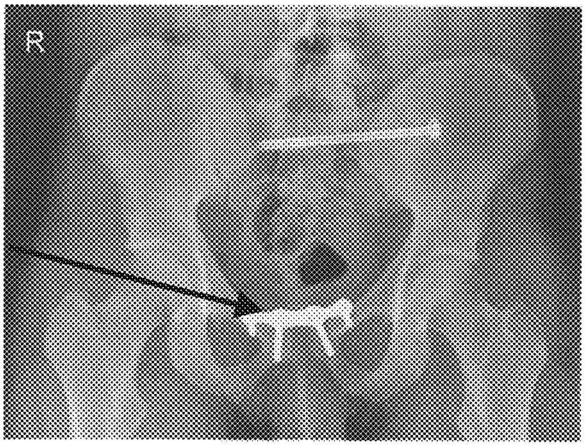
FIG. 3 shows an x-ray image of the pelvic region of a recipient of a rigid implant plate known from the prior art.

FIG. 3 shows an example of an X-ray image obtained from the pubic region of a human subject that has received a pubic symphysis rigid implant plate like the rigid implant played shown in FIG. 2. The position of the implant plate is indicated in each of FIGS. 2 and 3 with a black arrow.

As previously explained, while the use of implant plates for surgical treatment to repair a disjoined pubic symphysis is presently resorted to as a standard solution, it has to deal with a number of post-operatory complications that result, among others, from the rigidity of the implant, including loosening of the screws and/or breakage of the implant plate. This can lead to pain episodes and to mechanical instability of the front part of the pelvis and can make necessary a subsequent operation to repair or replace the damaged implant.

The present invention provides an implant device, an implant system and an implantation method that avoids such post-operatory complications.

Figure 4:
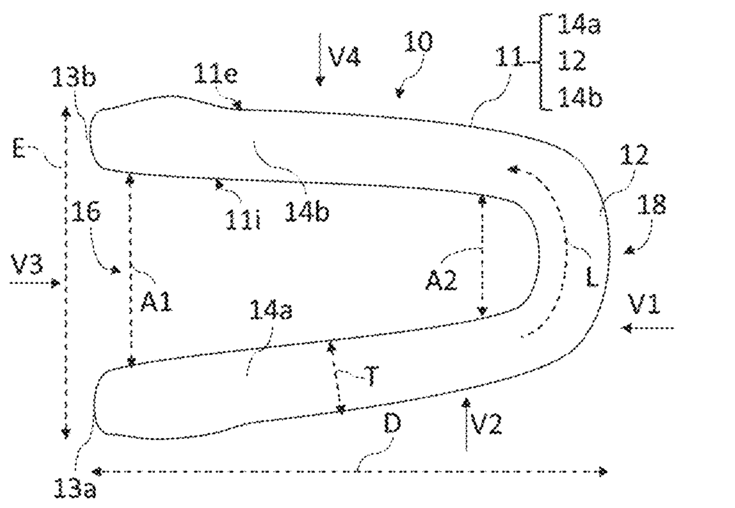
FIG. 4-8 show different schematic views of an implant device according to an embodiment of the invention.
Figure 5:
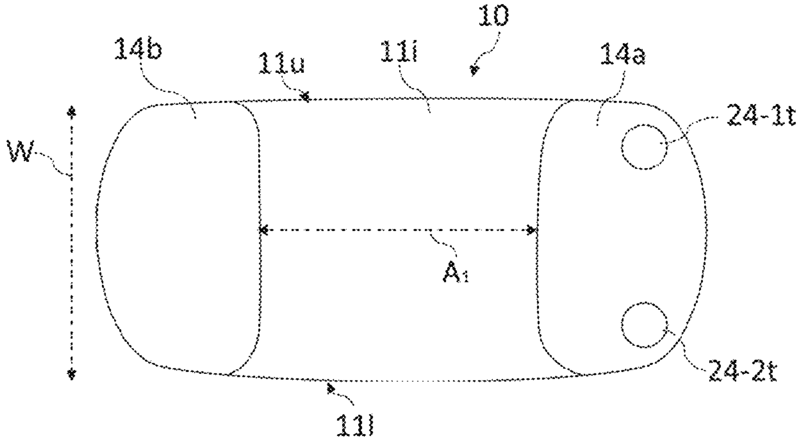
Figure 6:
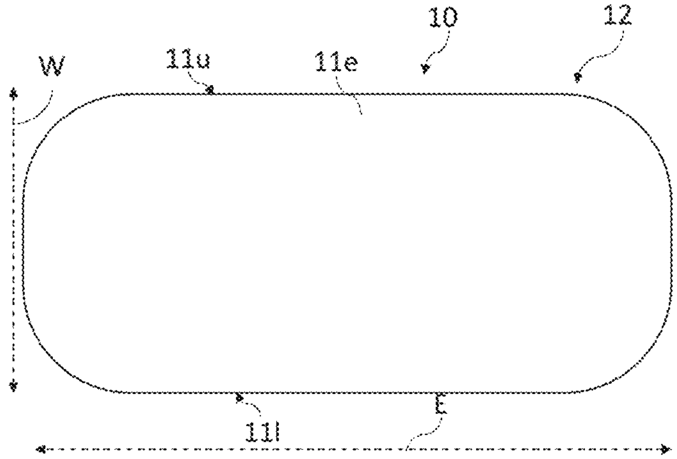
Figure 7:
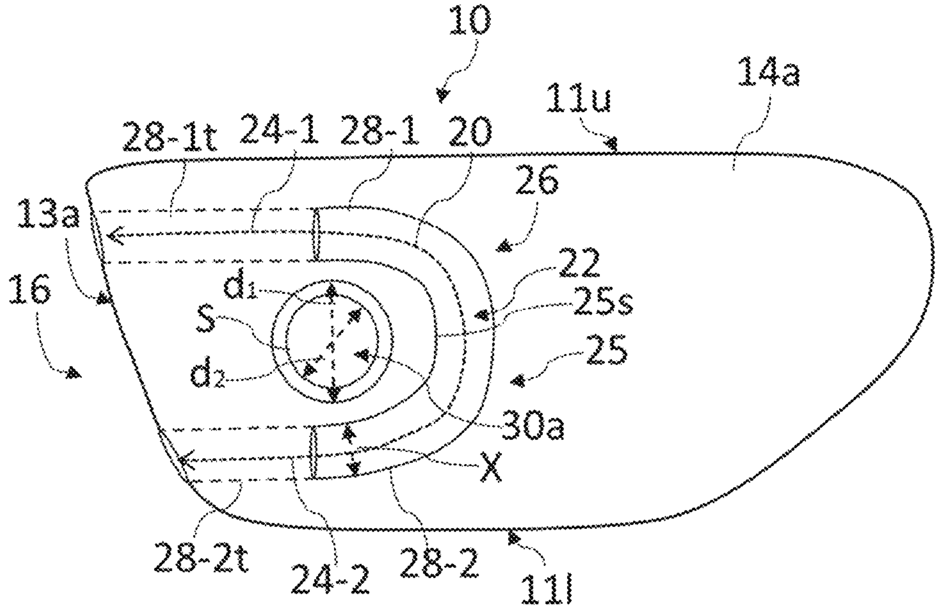
Figure 8:
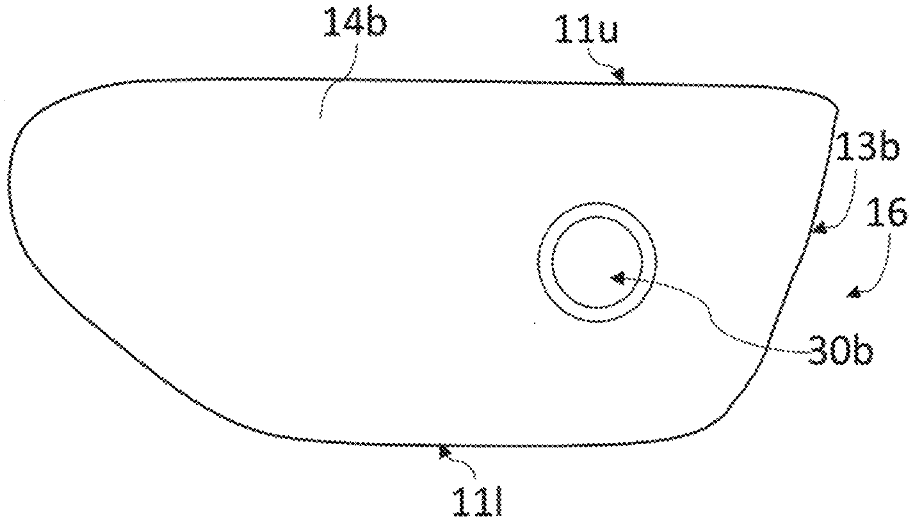
Figure 9:
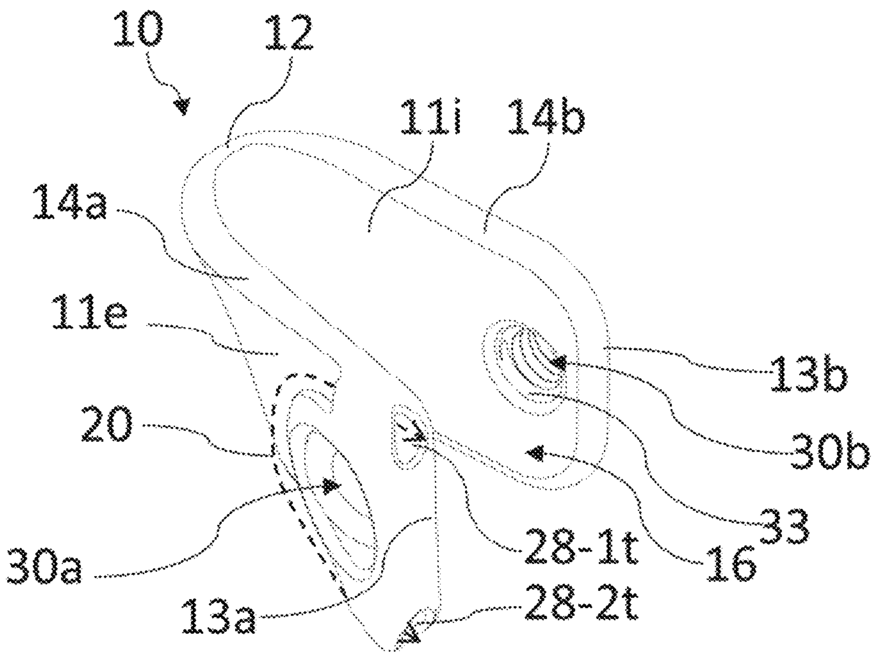
FIG. 9-10 show schematic perspective views of an implant device according to an embodiment of the invention, similar to the embodiment shown in FIGS. 4-8.
Figure 10:
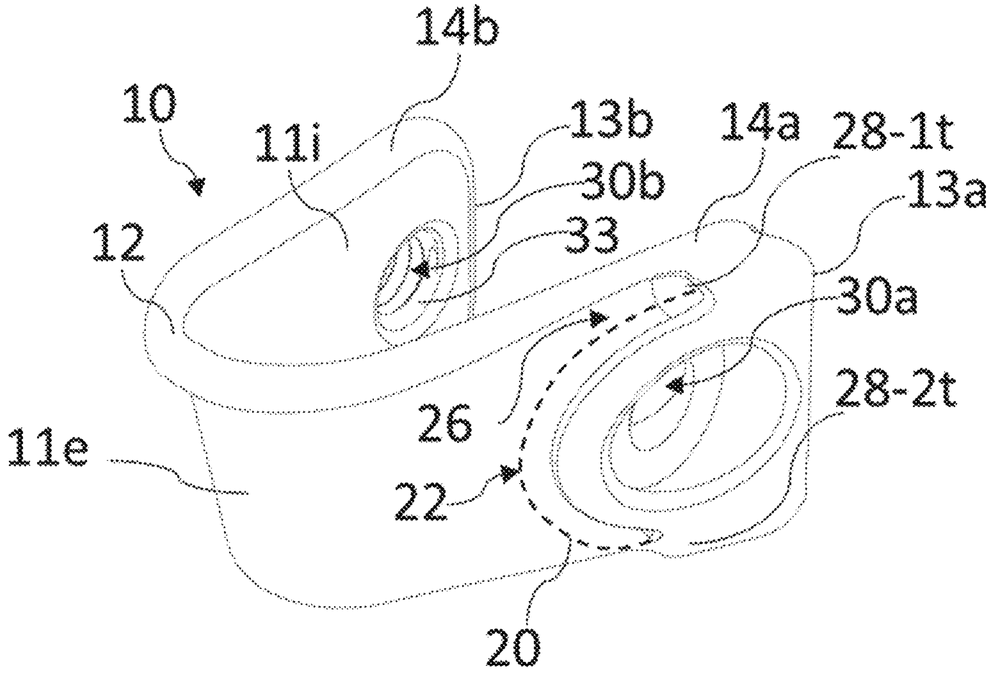

FIGS. 4 to 8 show different schematic views of an implant device 10 according to an embodiment of the invention. FIG. 4 shows a top (or bottom) view of the implant device 10. FIG. 5 shows a front side view from a perspective corresponding to a direction V3 indicated in FIG. 4 with an arrow. FIG. 6 shows a back side view from a perspective corresponding to a direction V1 indicated in FIG. 4 with an arrow. FIGS. 7 and 8 show lateral side views from perspectives respectively corresponding to directions that are indicated in FIG. 4 as directions V2 and V4. FIGS. 9 and 10 show perspective views of an implant device 10 based on the configuration described with respect to FIGS. 4 to 8. FIGS. 4 to 10 may be best understood when considered in combination.

The implant device 10 comprises a bent body 11 that extends curvedly along a longitudinal direction L from a first longitudinal end 13*a* at a first lateral arm 14*a* to a second longitudinal end 13*b* at a second lateral arm 14*b*. The bent body comprises a curved middle portion 12 that joins and connects the lateral arms 14*a* and 14*b*, which extend away from the middle portion 12. As seen in FIG. 4, the bent body 11 defines, as seen from a top view, a U-shape or C-shape, with an open end 16 extending between the first lateral arm 14*a* and the second lateral arm 14*b* at the respective longitudinal ends 13*a*, 13*b*. The open end 16 is opposite to a closed end 18 of the bent body in, which is defined by the middle portion 12.

In the embodiment shown, the lateral arms 14*a*, 14*b* extend from the middle portion 12 to the open end 16 in front of each other but without being strictly parallel to each other. Instead, they are slightly tilted outwards with respect to an imaginary central axis of mirror symmetry that could be drawn in the top view of FIG. 4 dividing the bent body 11 in a upper half and a lower half. The lateral arms 14*a*, 14*b* hence define an angle (not indicated in FIG. 4) with respect to each other (corresponding to twice the angle each of the lateral arms 14*a*, 14*b* defines with respect to the aforesaid imaginary central axis of mirror symmetry) that can be of about 20°. Therefore, a separation distance between the two lateral arms 14*a*, 14*b* increases continuously and monotonously from the closed end 18 towards the open end 16. The separation distance is maximal right at the open end 16, and can for example amount to a separation distance A1 of 17 mm. Closer to the closed and 18, the separation distance A2 between the two lateral arms 14*a*, 14*b* can for example be of 14 mm.

In the embodiment shown, the bent body 11 has a thickness T of 5 mm, a maximal distance D between the exterior surface ne of the middle portion 12 at the closed end 18 and the open end 16 of 30 mm, and a maximal separation distance E between the exterior surfaces 11*e* of both lateral arms 14*a*, 14*b* of 22 mm. In the example under consideration, the longitudinal extension of the bent body 11 along the longitudinal direction L from the first longitudinal end 13*a* to the second longitudinal end 13*b* is 50 mm.

In the exemplary embodiment shown in FIGS. 4 to 12, the bent body 11 is formed as a one-piece body made of titanium (Ti-6Al-4V) fabricated by metal-based 3D printing.

FIG. 5 shows a front side view of the implant device 10 as seen from the direction V3 indicated in FIG. 4. From this perspective, the lateral arms 14*a*, 14*b* are seen from the open end 16 and the middle portion 12, in particular the part of the middle portion corresponding to the inner surface 11*i* of the bent body 11 is seen through the open end 16.

FIG. 6 shows a back view of the implant device 10 as seen from the direction V1 indicated in FIG. 4. From this perspective, only the exterior surface 11*e* of the bent body 11 can be seen. In the embodiment under consideration, a width W of the bent body 11, i.e. a distance in a transverse direction perpendicular to the longitudinal direction and separating one (upper) transverse end nu of the bent body from the other (lower) transverse end 11*l* of the bent body 11 is 16 mm.

FIG. 7 shows a side view of the implant device 10 from a perspective in the direction V2 indicated in FIG. 4. In the side view of FIG. 7, only one lateral arm 14*a* is seen, while the other lateral arm 14*b* cannot be seen from this perspective. As seen in FIG. 7, a through-opening 30*a* and a guiding channel 26 are formed on the lateral arm 14*a*.

The through-opening 30*a* has a stepped profile with a first (outer) diameter $d_1$ of 7 mm and a second (inner) diameter $d_2$ of 4 mm. The first diameter $d_1$, which is smaller than the second diameter $d_2$, is closer to the exterior surface 11*e* of the bent body than the second diameter $d_2$. A shoulder S forms the transition from the first diameter $d_1$ to the smaller second diameter $d_2$.

The through-opening 30*a* allows a fixation bolt or screw having appropriate dimensions to penetrate through the bent body 11, cover the distance separating the lateral arms 14*a* and 14*b*, and penetrate through the second through-opening 30*b* formed in the other lateral arm 14*b* (not visible in FIG. 7, but shown in FIG. 8, as well as in FIGS. 9 and 10).

Figure 21:
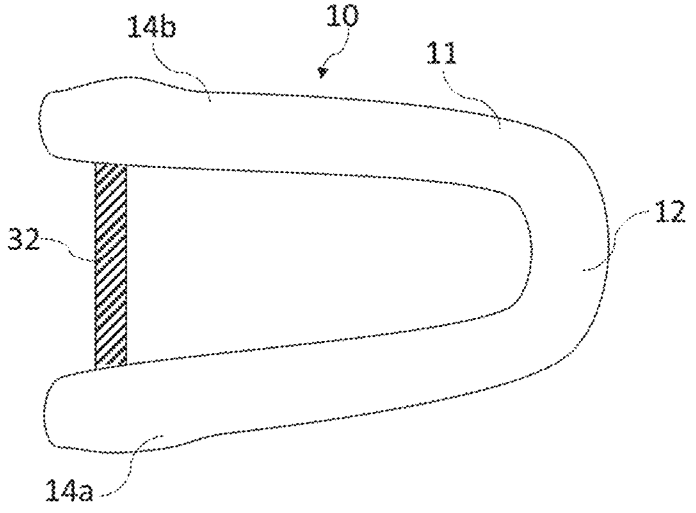
FIG. 21 shows a schematic top or bottom view of an implant device according to embodiments of the invention with a fixation screw passed therethrough.

FIG. 21 shows a variation of FIG. 4, in which a fixation screw 32 is received in the bent body 11 passing through the through-openings 30*a* and 30*b* of the lateral arms 14*a* and 14*b*, respectively. In such situation, a screw head of the screw 32 can rest on the shoulder S indicated in FIG. 7, which can operate as a stopper to prevent the screw 32 from being overscrewed through the through-opening 30*a*. As seen for example in FIGS. 9 and 10, the through-opening 30*b* can be threaded, i.e. can have an inner threaded profile 33 correspondingly adapted to the screw 32 (see FIG. 21), such that the screw 32 coming from the through-opening 30*a* can screw into the through-opening 30*b* and fixated therein.

Referring back to FIG. 7, the guiding channel 26 is a guiding element that defines a corresponding guiding path 20 on the lateral arm 14*a*. The guiding path 20, which is schematically indicated in FIG. 7 with a dashed double arrow, determines a curved trajectory around the through-opening 30*a* that a tensioning element such as a tensioning cable or the like follows when being guided along the guiding channel 26. The guiding channel 26 has a channel vertex 25 that defines a corresponding path vertex 22. The guiding channel 26 further has two channel portions 28-1, 28-2, each of them extending from the channel vertex 25 to the open end 16 around the through-opening 30*a* on a respective side of the through-opening 30*a*.

The channel portions 28-1 and 28-2 of the guiding channel 26 define respective path portions 24-1 and 24-2, which correspondingly extend from the path vertex 22 to the open end 16 around the through-opening 30*a* on a respective side of the through-opening 30*a*. The through-opening 30*a* is hence surrounded by the open end 16 as well as by the guiding channel 26. Consequently, a tensioning element such as a tensioning cable can be received within the guiding channel 26 such that the through-opening 30*a* is surrounded by the open end 16 and by the guiding path 20 followed by the tensioning element.

For a part of its extension, the guiding channel 26 is formed as a recess formed on the exterior surface 11*e* of the bent body 11 having a channel width X of 1.9 mm and a channel depth of 1.9 mm (not indicated in FIG. 7) perpendicular to the width X. However, at the open end 16, both channel portions 28-1 and 28-2 have a corresponding portion formed as a passage hole 28-1*t*, 28-2*t* tunnelling through the bent body 11.

FIGS. 9 and 10 show perspective views of an implant device 10 according to a related embodiment of the invention based on the configuration schematically illustrated in FIG. 4 to 8, in particular with respect to the configuration of the guiding channel 26 and the through-openings 30*a*, 30*b*. The implant device 10 shown in FIGS. 9 and 10 thus reproduces most features of the embodiment shown in FIGS. 4 to 8, which are indicated with the same reference signs. FIGS. 9 and 10 show perspective views of the implant device 10 from different sides. In FIG. 9, the through-opening 30*a* formed in the lateral arm 14*a* can be seen at the front and the through-opening 30 be formed in the other lateral arm 14*b* can be seen at the back. Each of the through-openings 30*a*, 30*b*, which are mutually aligned, communicate the exterior surface 11*e* of the bent body 11 with its internal surface 11*i*. In other related embodiments a partial opening may be formed in the second lateral arm 14*b* instead of the through-opening 30*b*. In the embodiment illustrated in FIGS. 9 and 10, the through-opening comprises a threaded inner profile 33 for receiving a screw coming from the through-opening 30*a*. In related embodiments, the through-opening 30*a* can also comprise such a threaded inner profile. In the perspective view of FIG. 9, which corresponds to a view of the bent body 11 from the open end 16, the tunnelling portions 28-1*t* and 28-2*t* of the guiding channel 26 can be seen at the longitudinal end 13*a* corresponding to the lateral arm 14*a*.

Figure 11:
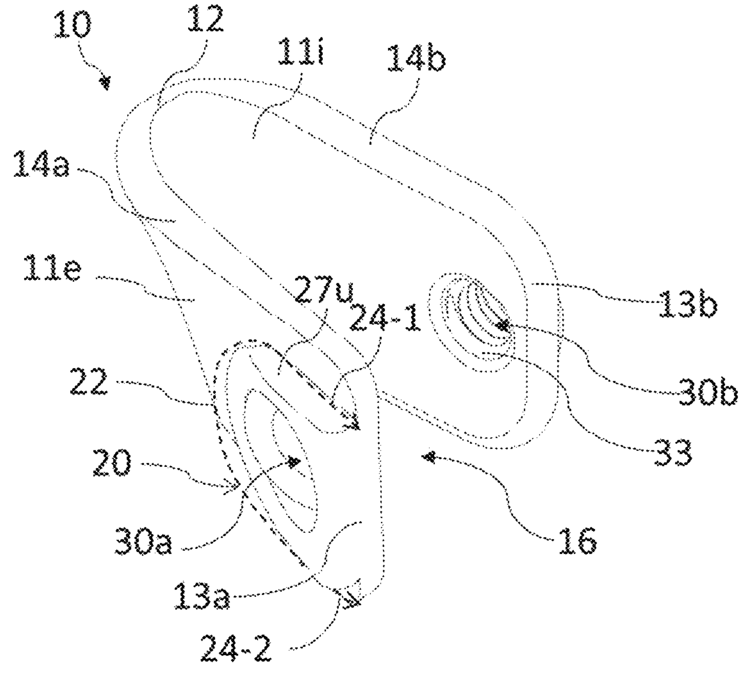
FIG. 11-12 show schematic perspective views of an implant device according to a related embodiment of the invention.
Figure 12:
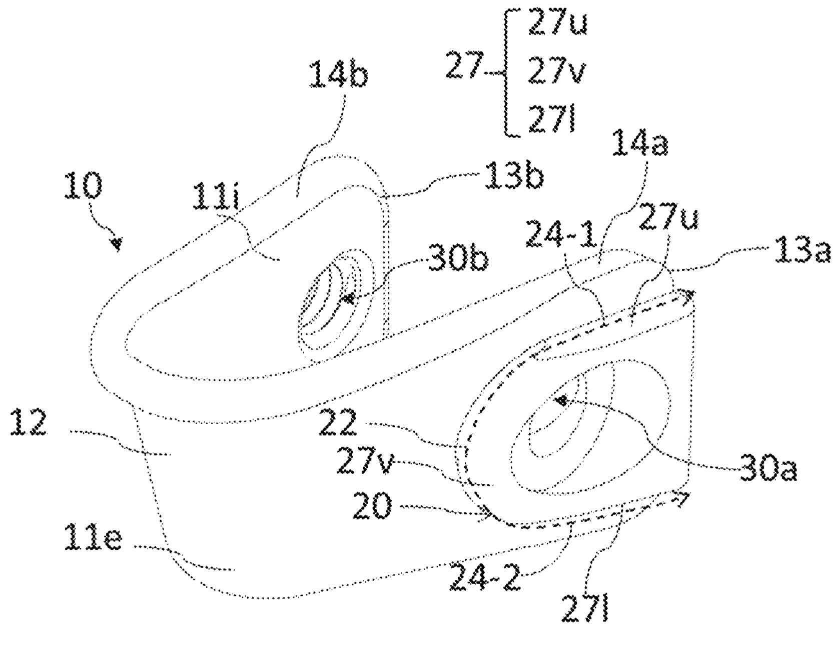

FIGS. 11 and 12 show perspective views of an implant device 10 according to a related embodiment, which basically differs from the embodiment illustrated in FIGS. 9 and 10 in that the guiding element formed in the lateral arm 14*a* is not formed as a guiding channel but instead as a guiding surface 27 that protrudes from the exterior surface 11*e* of the bent body 11. The guiding surface 27 is formed by an upper guiding surface 27*u* that extends completely perpendicular to the exterior surface 11*e* and defines the path portion 24-1, a lower guiding surface 27*l* that extends completely perpendicular to the exterior surface 11*e* and defines the path portion 24-2, and by a vertex guiding surface 27V that extends having a component perpendicular to the exterior surface 11*e* and facing away from the open end 16, which defines the path vertex 22. In other related embodiments, one or more guiding pins could be formed on the bent body instead of the guiding surface 27 or in addition to it.

Both in the embodiment illustrated in FIGS. 9 and 10, which has a guiding channel 26 as a guiding element, and in the embodiment illustrated in FIGS. 11 and 12, which has a guiding surface 27 as a guiding element, the corresponding guiding element protrudes from the exterior surface ne (cf. protruding guiding surface 27 in FIGS. 11 and 12) and/or recesses into the exterior surface 11*e* (cf. recessed portion of guiding channel 26 in FIG. 4 to 10), thereby forming a support surface (cf. inner surface 25*s* of the channel vertex 25 of FIG. 7 and vertex guiding surface 27V in FIGS. 11 and 12) that extends at least in part perpendicularly to the exterior surface 11*e* of the bent body 11 and at least in part facing away from the open end 16. Thereby, the guiding element allows in each case a tensioning element such as a tensioning cable guided along the corresponding guiding path 20 to transmit a tensioning force applied to it to the implant device 10.

For example, the guiding channel 26 of the embodiment illustrated in FIGS. 9 and 10 allows receiving a tensioning element (e. g. fixation cable 40 in FIG. 24 to 34) therein, such that the tensioning element is arranged within the recess formed by the guiding channel 26 and passing through the passage holes 28-1*t* and 28-2*t*. When such a tensioning element is guided along the guiding channel 26, the tensioning element can transmit a tension applied to it to the implant device 10 as a pulling force acting upon the implant device 10, in particular (but not only) upon the support surface 25*s* corresponding to the inner surface of the channel vertex 25 (cf. FIG. 7). Further, the passage holes 28-1*t* and 28-2*t* hold the tensioning element in place and prevent it from accidentally sliding off the guiding channel 26.

Figure 13:
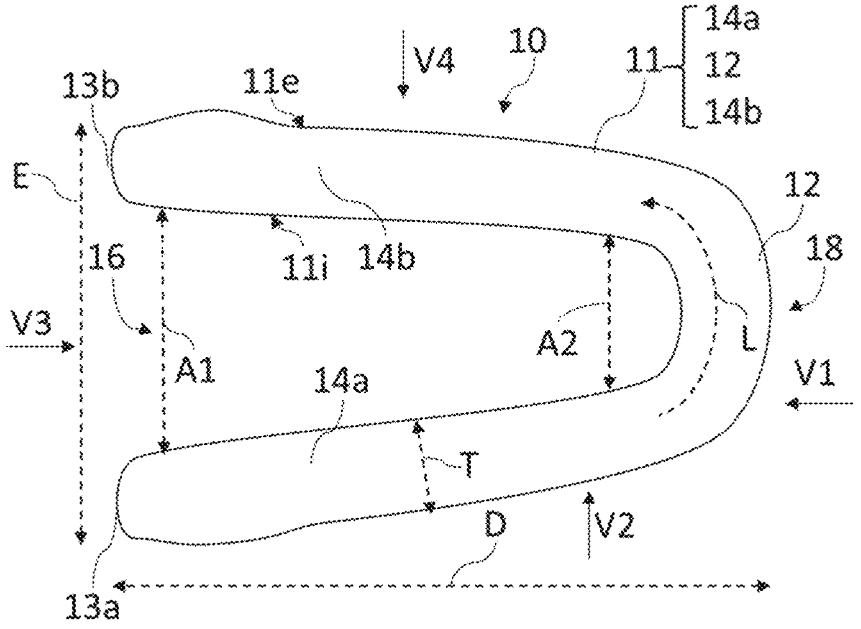
FIG. 13-17 show different schematic views of an implant device according to an embodiment of the invention.
Figure 16:
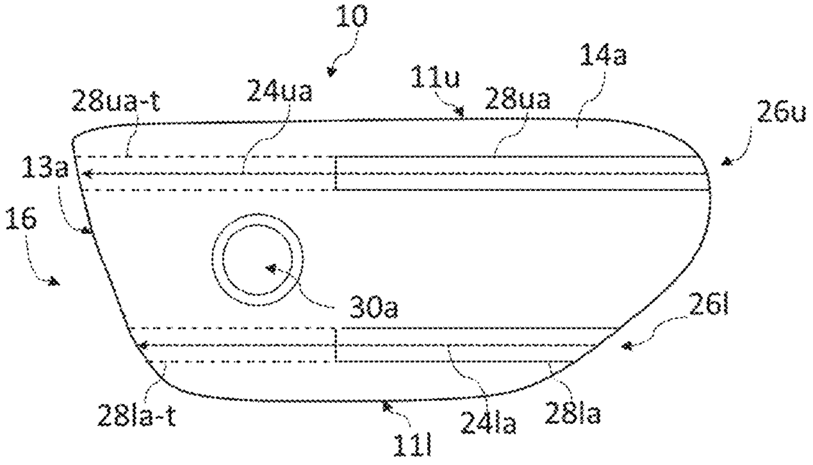
Figure 17:
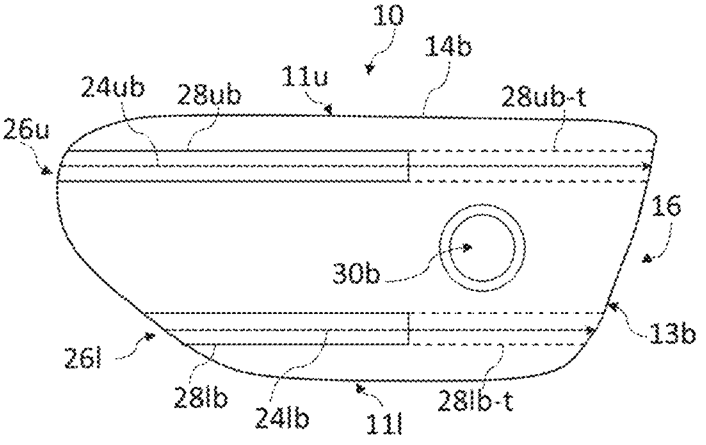
Figure 18:
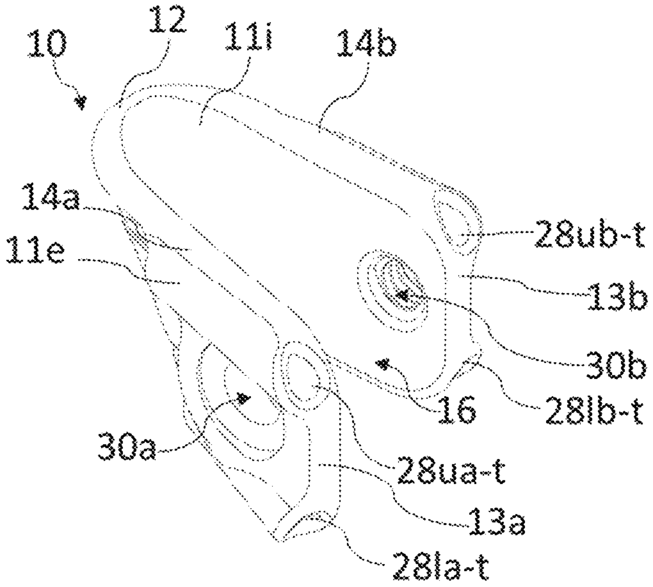
FIG. 18-19 show schematic perspective views of an implant device according to an embodiment of the invention, similar to the embodiment shown in FIG. 13-17.
Figure 19:
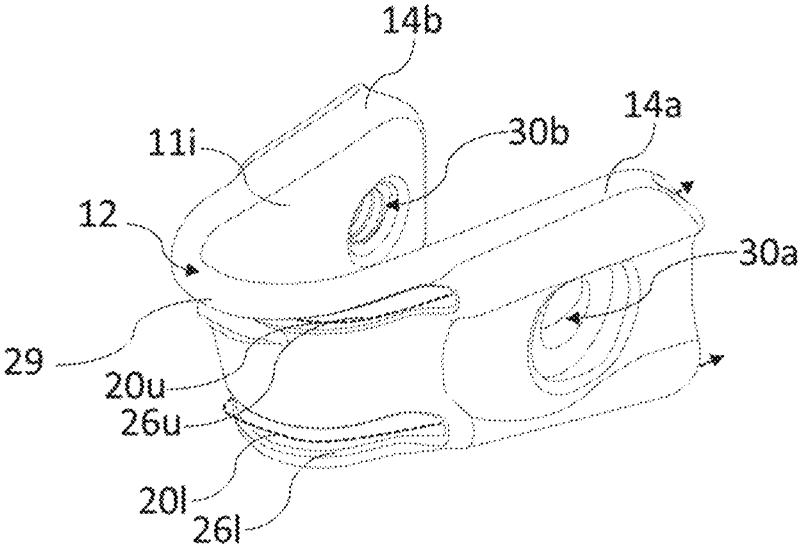
Figure 20:
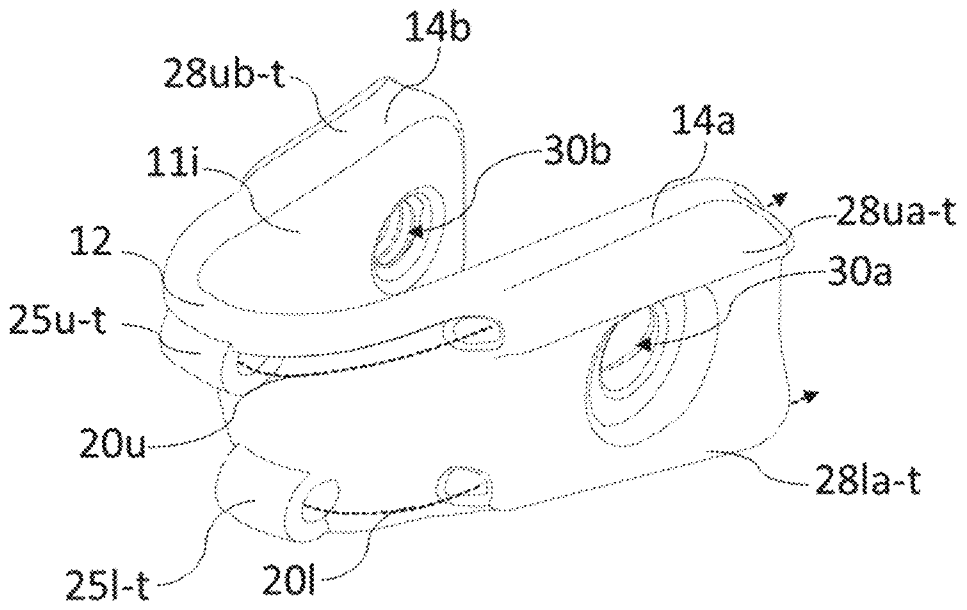
FIG. 20 shows a schematic perspective view of an implant device according to a related embodiment of the invention.

FIGS. 13 to 17 show different schematic views of an implant device 10 according to another embodiment of the invention, which can have the same dimensions that have been previously described for the embodiment discussed with respect to FIG. 4 to 8. FIG. 13 shows a top (or bottom) view, which is no different from the view of FIG. 4. FIGS. 18 and 19 show perspective views of an implant device 10 based on the configuration described with respect to FIGS. 13 to 17. The implant device 10 shown in FIGS. 18 and 19 thus reproduces most features of the embodiment described with respect to FIGS. 13 to 17, which are indicated with the same reference signs. FIG. 20 shows a perspective view of an implant device 10 according to a related embodiment.

Figure 14:
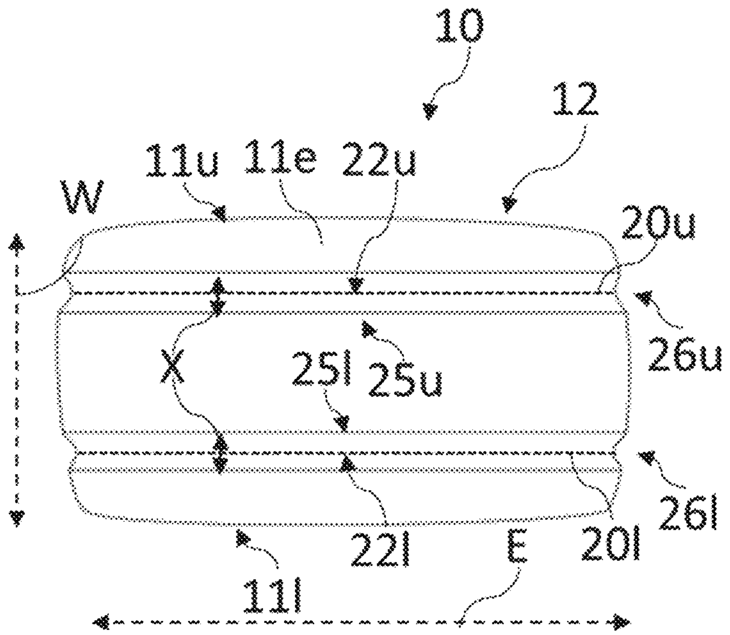
Figure 15:
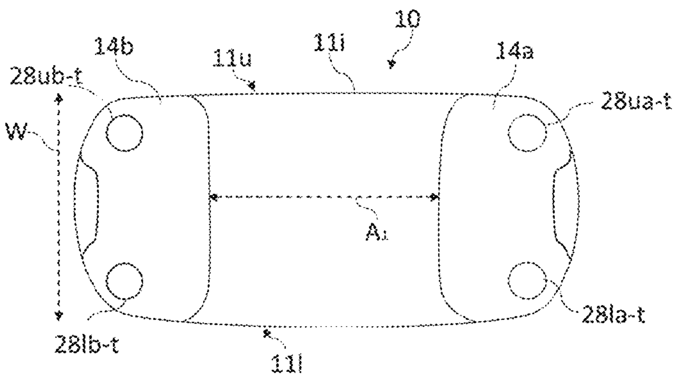

FIG. 14 shows a back side view in a perspective corresponding to the direction V1 indicated in FIG. 14, which basically corresponds to the back side view shown in FIG. 6. FIG. 15 shows a front side view from the direction V3 indicated in FIG. 14, which corresponds to the view used for FIG. 5. FIGS. 16 and 17 show lateral views respectively corresponding to perspectives from the directions indicated as V2 and V4 in FIG. 14, which correspond to the views used for FIGS. 7 and 8.

As seen in FIGS. 14, 16 and 17, one difference between the implant device 10 shown in FIGS. 13 to 17 and the implant device 10 shown in FIGS. 4 to 8 is that, in the embodiment shown in FIGS. 13 to 17, the implant device 10 comprises a first (upper) guiding element, formed as a first (upper) guiding channel 26*u*, and a second (lower) guiding element, formed as a second (lower) guiding channel 26*l*. As seen in FIGS. 14, 16 and 17, each of the first and second guiding channels 26*u*, 26*l* extends from the open end 16 on one of the lateral arms 14*a* (cf. FIG. 16) all along the longitudinal extension of the bent body 11—in the longitudinal direction L—to the open end 16 on the other lateral arm 14*b* (cf. FIG. 17), over the middle portion 12 (cf. FIG. 14), i.e. from one longitudinal end 13*a* to the other longitudinal end 13*b*.

The guiding channels 26*u* and 26*l* are guiding elements that respectively define an upper guiding path 20*u* and a parallel lower guiding path 20*l*. The guiding paths 20*u* and 20*l* are schematically indicated in FIGS. 14*m* 16 and 17 with dashed double arrows. The vertex 25*u* of the upper guiding channel 26*u* and the vertex 25*l* of the lower guiding channel 26*l* are formed in the middle portion 12 of the bent body 11 (cf. FIG. 14) and define the corresponding vertices 22*u* and 221 of the upper and lower guiding paths 20*u*, 20*l*, respectively.

Each of the guiding channels 26*u*, 26*l* has two channel portions 28*ua*, 28*ub* and 281*a*, 281*b* respectively (cf. FIGS. 16 and 17), each extending on one side of the respective vertex 25*u*, 25*l* and on one respective lateral arm 14*a* or 14*b* away from the middle portion 12 to the open end 16. The channel portion 28*ua* of the upper guiding channel 26*u*, which defines a path portion 24*ua* of the upper guiding path 20*a*, and the channel portion 281*a* of the lower guiding channel 26*l*, which defines a path portion 241*a* of the lower guiding path 20*l*, extend on the lateral arm 14*a* all the way to the longitudinal end 13*a* (cf. FIG. 16). The channel portion 28*ub* of the upper guiding channel 26*u*, which defines a path portion 24*ub* of the upper guiding path 20*a*, and the channel portion 281*b* of the lower guiding channel 26*l*, which defines a path portion 241*b* of the lower guiding path 20*b*, extend on the lateral arm 14*b* all the way to the longitudinal end 13*b* (cf. FIG. 17). Thus, on each other lateral arms 14*a*, 14*b*, a respective through-opening 30*a*, 30*b* formed therein is arranged between the upper guiding channel 26*u* and the lower guiding channel 26*l* and hence between the upper guiding path 20*u* and the lower guiding path 20*l*. The upper guiding channel 20*u* is formed proximal to the upper transverse edge 11*u* of the bent body 11 and the lower guiding channel 20*l* is formed proximal to the lower transverse edge 11*l* of the bent body 11.

As seen in FIGS. 14, 16 and 17, each of the guiding channels 26*u*, 26*l* is formed as a recess on the exterior surface 11*e* of the bent body 11 throughout a part of their extension, having a width X of 19 mm and a depth of 0.8 mm recessing into the exterior surface 11*e*. At the open end 16, each of the guiding channels 26*u*, 26*l* has on each of the lateral arms 14*a*, 14*b*, corresponding portions that are formed as passage holes 28*ua-t*, 28*ub-t*, 28*la-t*, 28*lb-t* tunnelling through the bent body 11 having a diameter of 19 mm. The upper guiding channel 26*u* comprises, at the open end 16 in both lateral arms 14*a*, 14*b*, respective passage holes 28*ua-t*, 28*ub-t* (cf. FIGS. 15 and 16) and the lower guiding channel 26*l* comprises, at the open end 16 in both lateral arms 14*a*, 14*b*, respective passage holes 28*la-t*, 28*lb-t* (cf. FIGS. 15 and 17).

FIGS. 18 and 19 show perspective views of an implant device 10 according to a related embodiment of the invention based on the configuration schematically illustrated in FIG. 13 to 17, in particular with respect to the configuration of the guiding channels 26*u*, 26*l* and the through-openings 30*a*, 30*b*. The implant device 10 shown in FIGS. 18 and 19 thus reproduces most features of the embodiment shown in FIGS. 13 to 17, which are indicated with the same reference signs. FIGS. 18 and 19 show perspective views of the implant device 10 from different sides. In FIG. 18, the through-opening 30*a* formed in the lateral arm 14*a* can be seen at the front and the through-opening 30 be formed in the other lateral arm 14*b* can be seen at the back. Each of the through-openings 30*a*, 30*b*, which are mutually aligned, communicate the exterior surface 11*e* of the bent body 11 with its internal surface iii. In other related embodiments a partial opening may be formed in the second lateral arm 14*b* instead of the through-opening 30*b*. In the embodiment illustrated in FIGS. 18 and 19, the through-opening comprises a threaded inner profile 33 for receiving a screw coming from the through-opening 30*a*. In related embodiments, the through-opening 30*a* can also comprise such a threaded inner profile.

In the perspective view of FIG. 18, which corresponds to a view of the bent body 11 from the open end 16, the tunnelling portions 28*ua-t*, 28*ub-t*, 28*la-t*, 28*lb-t* of the guiding channels 26*u*, 26*l* can be seen at the respective longitudinal ends 13*a* and 13*b* corresponding to the lateral arms 14*a* and 14*b* respectively.

Also indicated in FIG. 19 is a protruding lip 29 formed as a protrusion from the exterior surface 11*e* of the bent body at the upper transverse edge 11*u* (cf. FIG. 14) in the middle portion 12, which prevents a tensioning element guided along the upper guiding channel 26*u* following the upper guiding path 20*u* from sliding off the upper guiding channel 26*u* and further provides an accessible feature that can be used by a surgeon for manipulating the implant device 10 during implantation.

As can be seen in FIGS. 18 and 19 (and in FIG. 9 to 12), the middle portion 12 of the bent body 11 is tilted at the closed end 18 with respect to the transverse direction, i.e. the direction from the lower transverse edge 11*l* to the upper transverse edge 11*u* (the vertical direction in each of FIGS. 16 and 17) on the lateral arms 14*a*, 14*b*. Thus, a separation distance between the exterior surface 11*e* of the bent body 11 at the middle portion 12 and the open end 16 increases in the transverse direction from the lower transverse edge nil towards the upper transverse and nu and is hence greater at the upper transverse edge nu than at the lower transverse and 11*l*. This implies that the upper guiding path 20*u* can be longer than the lower guiding path 20*l*. This tilted form of the middle portion 12 is due to anatomic reasons and serves the purpose of better adapting to the form of a pelvic bone.

FIG. 20 shows a perspective view of an implant device 10 according to a related embodiment, which basically differs from the embodiment illustrated in FIGS. 18 and 19 in that the guiding elements are formed as tunnelling portions recessing from the external surface 11*e* without including any portions recessing into the external surface 11*e*. The upper guiding path 20*u* is defined by three tunnelling portions: by two lateral tunnelling portions 28*ua-t* and 28*ub-t*, which are identical to the tunnelling portions 28*ua-t* and 28*ub-t* of the embodiment illustrated in FIGS. 18 and 19, and by a vertex tunnelling portion 25*u-t* that is formed as an eyelet at the middle portion 12, proximal to the upper transverse edge nu of the bent body (cf. FIG. 14). The lower guiding path 20*l* is defined by three tunnelling portions: by two lateral tunnelling portions 28*la-t* and 28*lb-t*, which are identical to the tunnelling portions 28*la-t* and 28*lb-t* of the embodiment illustrated in FIGS. 18 and 19, and by a vertex tunnelling portion 25*l-t* that is formed as an eyelet at the middle portion 12, proximal to the lower transverse edge nil of the bent body (cf. FIG. 14).

Both in the embodiment illustrated in FIGS. 18 and 19, which has the guiding channels 26*u*, 26*l* as guiding elements, and in the embodiment illustrated in FIG. 20, which has the tunnelling portions 28*ua-t*, 25*u-t*, 28*ub-t*, 28*la-t*, 25*l-t*, 28*lb-t* as guiding elements, the corresponding guiding elements protrude from the exterior surface 11*e* (cf. tunnelling portions 25*u-t*, 25*l-t*) and/or recesses into the exterior surface 11*e* (cf. guiding channels 26*u*, 26*l*), thereby forming support surfaces (cf. inner walls of the tunnelling portions 28*ua-t*, 25*u-t*, 28*ub-t*, 28*la-t*, 25*l-t*, 28*lb-t*) that extend at least in part perpendicularly to the exterior surface 11*e* of the bent body 11 and support surfaces that face away from the open end 16 (cf. portions of the respective guiding elements formed in the middle portion 12). Thereby, the guiding elements 26*u*, 26*l*, 28*ua-t*, 25*u-t*, 28*ub-t*, 28*la-t*, 25*l-t*, 28*lb-t* allow in each case a tensioning element such as a tensioning cable guided along the corresponding guiding paths 20*u*, 20*l* to transmit a tensioning force applied to it to the implant device 10 and hold the tensioning cable in place, preventing it from sliding off the corresponding guiding path 20*u* or 20*l*.

FIG. 21 shows a top (or bottom) view of an implant device 10, which may correspond to the implant device seen in FIG. 4 or 13, wherein a fixation screw 32 is received through the bent body 11, passed through through-openings 30*a*, 30*b* (not shown in FIG. 21) that are formed on each of the lateral arms 14*a*, 14*b*.

Figure 22:
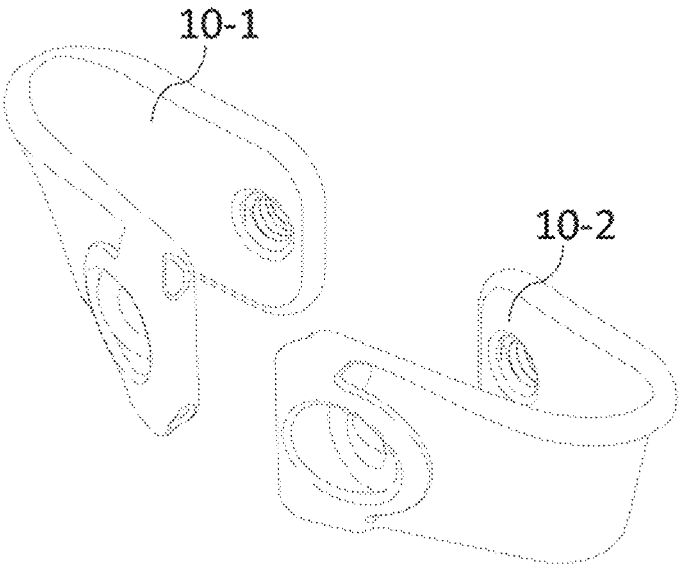
FIG. 22, 23 show pairs of substantially mirror-symmetric implant devices that can be comprised in an implant system according embodiments of the invention.

FIG. 22 shows a first implant device 10-1 and a second implant device 10-2 forming a complementary pair of "partner" implant devices than can be comprised in an implant system according to the invention. The first and second implant devices 10-1, 10-2 both implant devices corresponding to the embodiment illustrated and described with respect to FIGS. 9*a* and 10. The first and second implant devices 10-1, 10-2 mirror symmetric with respect to each other (but for the threaded profiles of the through-openings 30*a*, 30*b*, if any) and have geometries and dimensions respectively adapted for fitting the left and right os pubis of the pelvis of a patient, in particular the medial part of the obturator foramen.

Figure 23:
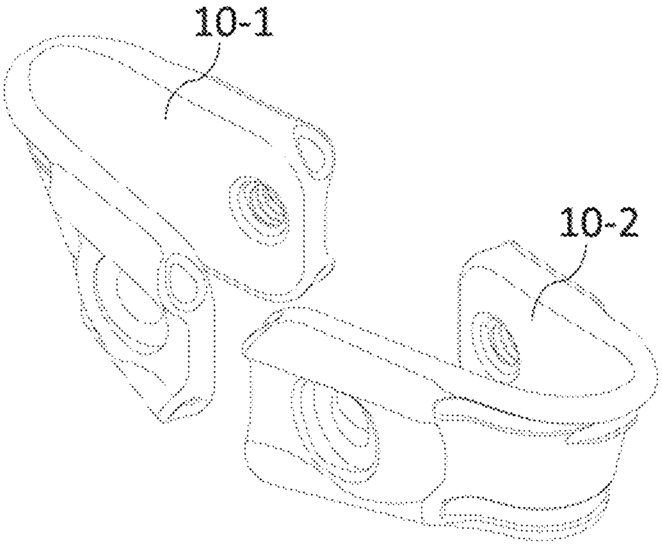

FIG. 23 shows a similar pair of "partner" implant devices 10-1, 10-2 but each corresponding to the embodiment illustrated and described with respect to FIGS. 18 and 19.

FIGS. 24 to 28 show different configurations of an implant device 50 according to the invention, comprising a first implant device 10-1 and a second implant device 10-2. Although the implant devices 10-1 and 10-2 of the implant systems 50 illustrated in FIGS. 24 to 28 are schematic simplified U-shaped implant devices, wherein the lateral arms extend in parallel to each other having a separation distance between them that is substantially constant, it is understood that any two implant devices according to the invention can be used instead, for example the implant devices 10-1, 10-2 shown in FIG. 22 or the implant devices 10-1, 10-2 shown in FIG. 23, but also two corresponding "partner" implant devices according to the embodiment illustrated and described with respect to any of FIG. 11-12 or 20 or to any other embodiment of the invention.

Figure 24:
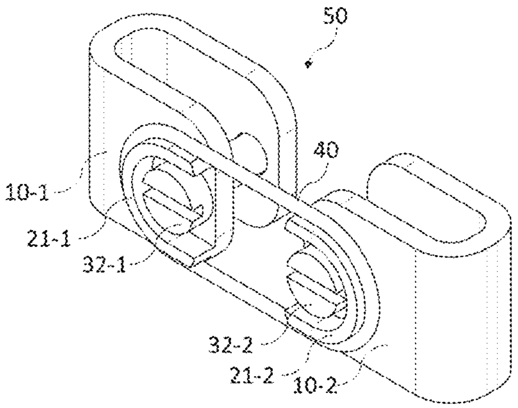
FIG. 24-28 schematically illustrate different arrangements of a tensioning element in an implant system according to embodiments of the invention.
Figure 25:
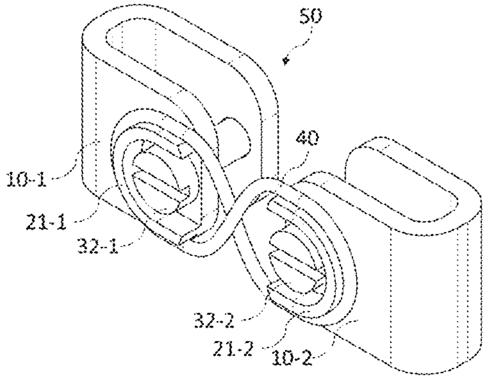

FIGS. 24 and 25 show an implant device 50 comprising first and second implant devices 10-1, 10-2 each comprising a guiding element 21-1, 21-2 protruding perpendicularly from the external surface of the corresponding bent body that is only formed in one of the lateral arms of the respective bent body. Each of the implant devices 10-1, 10-2 has a respective fixation screw 32-1, 32-2 passed through the through-openings thereof. Each of the guiding elements 21-1, 21-2 defines a corresponding support surface on which a tensioning element 40, in this case a metallic tensioning cable, can rest when being guided along the guiding paths defined by the guiding elements 21-1 and 21-2. When the tensioning element 40 is tensioned, it abuts against the support surfaces defined by the guiding elements 21-1 and 21-2 thereby pulling the implant devices 10-1 and 10-2 towards each other. In the configuration shown in FIG. 24, the tensioning element 40 is arranged simply forming a simple loop, whereas in the configuration shown in FIG. 25, the tensioning element 40 is arranged forming a double loop or an 8-shape, being twisted around once between both implant devices 10-1 and 10-2. Both in the configuration shown in FIG. 24 and in the configuration shown in FIG. 25, the tensioning element 40 extends on one of the lateral arms of each of the implant devices 10-1, 10-2 only, without extending on the other lateral arm of each of the implant devices 10-1, 10-2.

Figure 26:
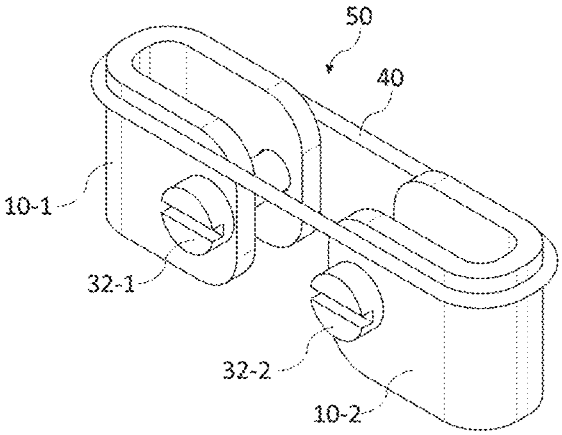

FIG. 26 illustrates a related embodiment of an implant system 50 comprising a first implant device 10-1 and a second implant device 10-2 comprising a respective guiding element that is formed as a guiding channel at one of the transverse edges of the corresponding bent body. In this configuration, the tensioning element 40 and closes both implant devices 10-1 and 10-2 extending on both lateral arms of each of the implant devices 10-1, 10-2.

Figure 27:
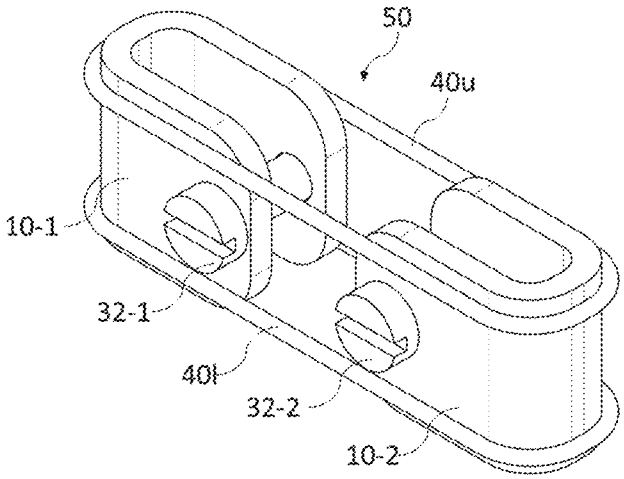

FIG. 27 illustrates a related embodiment of an implant system 50 comprising a first implant device 10-1 and a second implant device 10-2, each of them comprising an upper guiding element formed as a guiding channel at an upper transverse edge of the corresponding bent body and a lower guiding element formed as a lower guiding channel at the lower transverse edge of the corresponding bent body. A first (upper) tensioning element 40*u* is guided along the guiding path defined by the upper guiding channel and a second (lower) tensioning element 401 is guided along the guiding path defined by the lower guiding channel.

Figure 28:
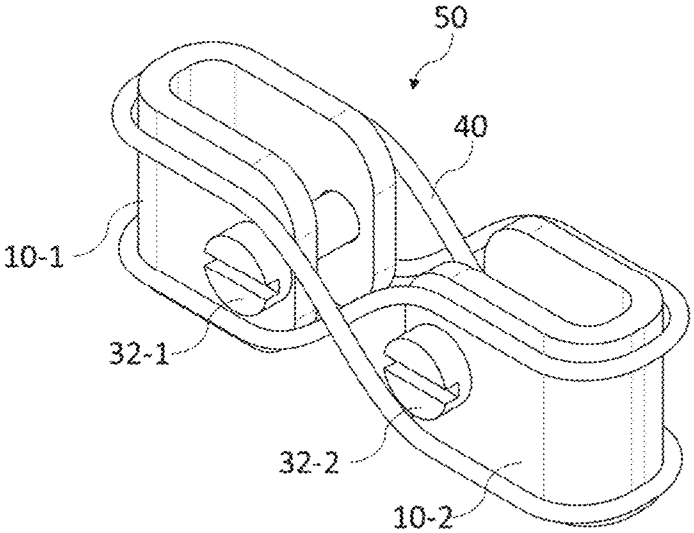

FIG. 28 illustrates the implant system 50 illustrated in FIG. 27 in a configuration in which a single tensioning element 40 is guided along the upper and lower guiding channels of each of the implant devices 10-1 and 10-2 being twisted around twice.

Figure 29:
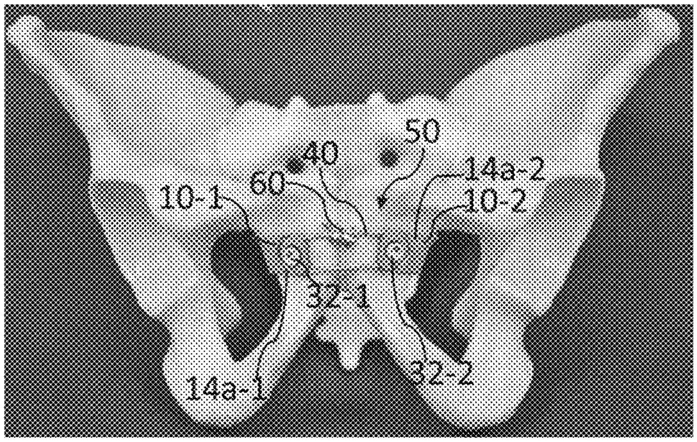
FIG. 29-31 shows an anatomic model of a re-joined pubic symphysis using an implant system according to an embodiment of the invention, which incorporates two implant devices like the implant device of FIG. 4-10.
Figure 30:
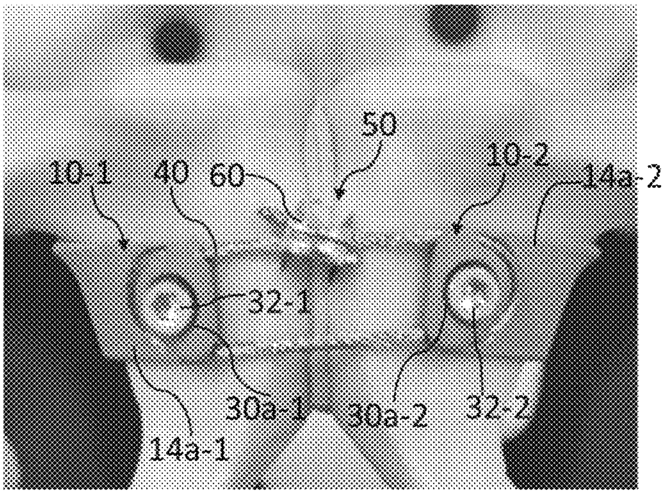
Figure 31:
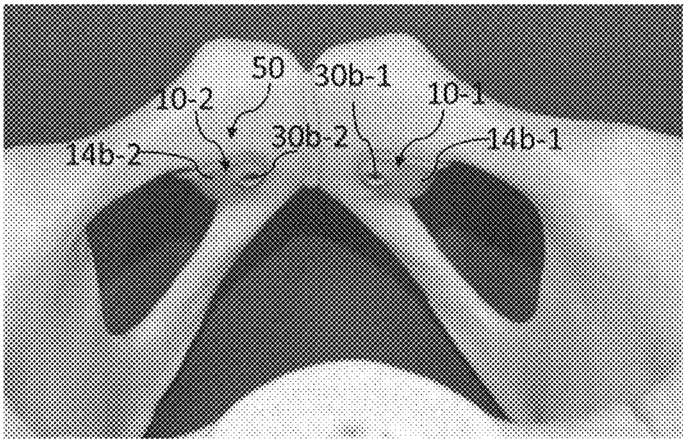

FIGS. 29 to 31 show an anatomic model of a human pelvis with a re-joined pubic symphysis using an implant system 50 according to an embodiment of the invention comprising a first implant device 10-1 and a second implant device 10-2, each corresponding to the implant device 10 of the embodiment shown in FIGS. 4 to 10, wherein the guiding channels are each formed as a recess on the exterior surface of the respective bent body having a depth of 1.9 mm and a width of 1.9 mm. FIG. 29 shows a front view of the pelvis. FIG. 30 shows a zoomed-in area of FIG. 29. FIG. 31 shows a dorsal view of the pelvis.

In the implant system 50 used in FIGS. 29 to 31, a tensioning element 40, which in the embodiment shown is a steel cable having a diameter of 1.7 mm, is received in the guiding channel of the first implant device 10-1 and in the guiding channel of the second implant device 10-2. Thus, when tension is applied to the tensioning element 40, the tensioning element 40 transmits the tension to the implant devices 10-1 and 10-2, which are arranged with their open ends 16 facing each other, and pulls them towards each other. The guiding channels of the implant devices 10-1 and 10-2 determine the respective trajectory of the tensioning element 40 around the implant devices 10-1, 10-2 and keep the tensioning element 40 in place when tension is applied to pull the implant devices 10-1, 10-2 towards each other.

Also shown in FIGS. 29 to 31 are a first fixation screw 32-1 passed through the through-openings 30*a*-1, 30*b*-1 of the first implant device 10-1 and a second fixation screw 32-2 passed through the through-openings 30*a*-2, 30*b*-2 of the second implant device 10-2. The first and second fixation screws 32-1, 32-2 have a nominal diameter of 4 mm and a spanner size of 7 mm.

The implant system 50 according to the invention can be used in a method of fixating together the left and right hemipelvises of a patient for re-joining a disjoined pubic symphysis. In order to do so, the first implant device 10-1 can be arranged around the left hemipelvis (wherein "left" and "right" refers to the perspective of the viewer of FIG. 29) around the corpus of the pubis of the left hemipelvis such that it is partly surrounded by the bent body 11 of the first implant device 10-1, with the left hemipelvis abutting against the interior surface of the first implant device 10-1 and the lateral arms **14*a*-1, 14*b*-1 of the first implant device 10-1 extending towards the pubic symphysis on opposed surfaces of the pelvis, one lateral arm 14*a*-1 being on a frontal side of the pelvis and the other lateral arm 14*b*-1** being on the dorsal side of the pelvis.

The first implant device 10-1 is fixated to the left hemipelvis using the fixation screw **32*a*, which passes through the through-opening 30*a*-1 formed in the lateral arm 14*a*-1 of the first implant device 10-1, extends across the left hemipelvis through a hole that a surgeon drills therein for that purpose, and passes through the through-opening 30*b*-1 formed in the other lateral arm 14*b*-1 of the first implant device 10-1**.

The second implant device 10-2 is arranged around the corpus of the right hemipelvis and fixated thereto using a second fixation screw **32-2*b*** in an analogous manner.

Then, the tensioning element 40, which is received in the guiding channel of the first implant device 10-1 and in the guiding channel of the second implant device 10-2, can be used for pulling both implant devices 10-1, 10-2 towards each other by tensioning the tensioning element 40. A cable crimp 60 can be used for tensioning the tensioning element 40 by regulating its tensioned length and for maintaining a desired level of tension once reached.

As seen in FIGS. 29 and 30, in this case the tensioning element 40 extends between the lateral arm **14*a*-1 of the first implant device 10-1 and the lateral arm 14*a*-2 of the second implant device 10-2 on the frontal side of the pubic symphysis but, as seen in FIG. 31, the tensioning element 40 does not extend between the other lateral arms 14*b*-1, 14*b*-2 of the first and second implant devices 10-1, 10-2, respectively, which are arranged on the dorsal side of the respective hemipelvis. In other words, the tensioning element 40 does not cross the respective obturator foramen. This corresponds to the configuration illustrated in FIG. 24, although the tensioning element 40 could instead be arranged according to the configuration illustrated in FIG. 25**.

Figure 32:
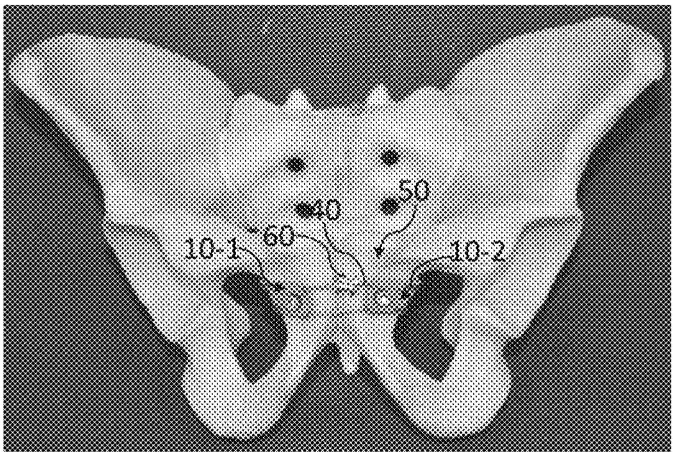
FIG. 32-34 shows an anatomic model of a re-joined pubic symphysis re-joined using an implant system according to an embodiment of the invention, which incorporates two implant devices like the implant device of FIG. 13-19.
Figure 33:
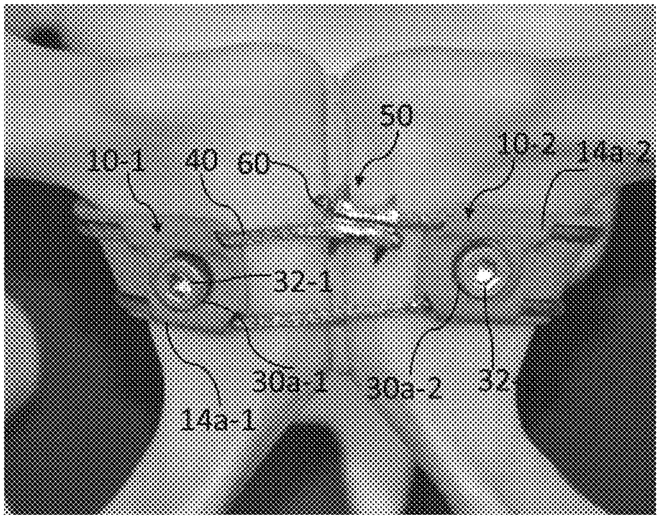
Figure 34:
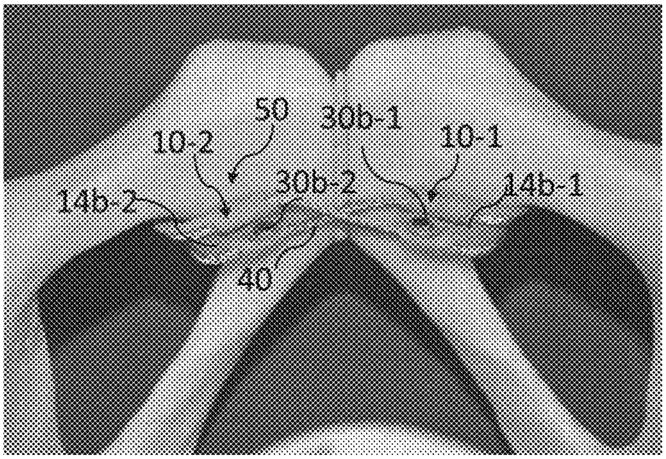

FIGS. 32 to 33 show an anatomic model of a human pelvis with a pubic symphysis re-joined according to a different method using a similar implant system 50 comprising a first implant device 10-1 and a second implant device 10-2, each corresponding to the implant device 10 of the embodiment shown in FIGS. 13 to 19. FIG. 32 shows a front view of the pelvis. FIG. 33 shows a zoomed-in area of FIG. 32. FIG. 34 shows a back view of the pelvis.

In the implant system 50 of FIGS. 32 to 34, the first and second implant devices 10-1, 10-2 can be attached to the left and right hemipelvises in the same manner that has been previously explained for the implant system 50 of FIGS. 25 to 27. However, in this case, since the implant devices 10-1, 10-2 have guiding channels that extend on both lateral arms **14*a*-1, 14*a*-2 and 14*b*-1, 14*b*-2 of the first and second implant devices 10-1, 10-2, respectively, the tensioning element 40 used for pulling both implant devices 10-1, 10-2 towards each other, which is received in the two (upper and lower) guiding channels of the first implant device 10-1 and in the two (upper and lower) guiding channels of the second implant device 10-2, extends both between the lateral arm 14*a*-1 of the first implant device 10-1 and the lateral arm 14*a*-2 of the second implant device 10-2 on the frontal side of the pubic symphysis (cf. FIGS. 32 and 33) and on the dorsal side of the pubic symphysis (cf. FIG. 34) between the lateral arm 14*b*-1 of the first implant device 10-1 and the lateral arm 14*b*-2 of the second implant device 10-2. Thus, in this case the tensioning element 40** crosses the left and right obturator foramen.

As seen in FIG. 34, the tensioning element 40 is twisted around once behind the pubic symphysis and hence defines an eight-shape, such that a single tensioning element 40 can be used and a higher stability against shear forces is achieved. However, in other embodiments it is possible to arrange the tensioning element 40 or two independent tensioning elements according to other configurations, for example according to any of the configurations illustrated in FIG. 27 or 28.

Although preferred exemplary embodiments are shown and specified in detail in the drawings and the preceding specification, these should be viewed as purely exemplary and not as limiting the invention. It is noted in this regard that only the preferred exemplary embodiments are shown and specified, and all variations and modifications should be protected that presently or in the future **11*e*** within the scope of protection of the invention as defined in the claims.

What is claimed is:

1. An implant system comprising:

a first implant device and a second implant device, each of the first implant device and the second implant device being configured for being fixated to a corresponding hemipelvis by form-fitting;

wherein each of the first implant device and the second implant device comprises:

a bent body comprising a curved middle portion and two lateral arms, wherein the two lateral arms extend away from the middle portion and are mutually joined by the middle portion, such that the bent body defines an open end between the two lateral arms opposite a closed end defined by the middle portion; and at least one guiding element defining at least one guiding path extending along at least a portion of the bent body, wherein each of the at least one guiding path comprises a path vertex and two path portions extending away from the path vertex and from the closed end of the bent body; and at least one tensioning element configured for pulling the first and second implant devices towards each other by tension by being guided along one or more of the at least one guiding path of the first implant device and along one or more of the at least one guiding path of the second implant device, such that the first and second implant devices pull both hemipelvises together and cause the pubic symphysis to re-join.

2. The implant system of claim 1, wherein a separation distance between the two lateral arms increases from the closed end towards the open end of the bent body.

3. The implant system of claim 1, wherein the bent body further comprises one or more through-openings connecting an exterior surface of the bent body with an interior surface of the bent body, wherein the one or more through-openings are formed in one or both of the lateral arms.

4. The implant system of claim 3, wherein at least one of the one or more through-openings is formed in one of the lateral arms and at least another one of the one or more through-openings is formed in the other lateral arm, wherein the through-opening in one of the lateral arms is aligned with the through-opening in the other one of the lateral arms; wherein said at least one of the one or more through-openings formed in one of the lateral arms and said at least another one of the one or more through-openings formed in the other lateral arm are configured for receiving a fixation element therethrough, such that the fixation element joins the two lateral arms.

5. The implant system of claim 1, wherein one or more of the at least one guiding element is formed at least in part protruding from and/or recessing into an exterior surface of the bent body.

6. The implant system of claim 1, wherein one or more of the at least one guiding element forms a support surface, wherein the support surface has at least a perpendicular component with respect to an exterior surface of the bent body and/or o faces away from the open end.

7. The implant system of claim 1, wherein the at least one guiding element comprises or is at least one guiding channel extending along at least a portion of the bent body, wherein each of the at least one guiding channel comprises a channel vertex and two channel portions extending away from said channel vertex and from the closed end, wherein said channel vertex corresponds to a path vertex of the at least one guiding path and said channel portions correspond to path portions of the at least one guiding path.

8. The implant device of claim 7, wherein the at least one guiding channel is formed at least in part as a recess on an exterior surface of the bent body.

9. The implant device of claim 7, wherein the at least one guiding channel is formed at least in part as a passage hole tunnelling through a portion of the bent body.

10. The implant system of claim 3, wherein the at least one guiding element is configured such that the path vertex of one or more of the at least one guiding path is formed in one of the lateral arms, wherein each of the corresponding path portions extends on said lateral arm away from the corresponding path vertex towards the open end of the bent body, wherein the path vertex is formed between the middle portion and a corresponding through-opening formed in said one of the lateral arms, wherein each of the path portions extends on said lateral arm away from the corresponding path vertex towards the open end of the bent body on one respective side of the corresponding through-opening, such that said corresponding through-opening is partly surrounded by the respective guiding path.

11. The implant system of claim 1, wherein the at least one guiding element is configured such that the path vertex of one or more of the at least one guiding path is formed in the middle portion of the bent body and each of the path portions on a respective one of the lateral arms away from the middle portion towards the open end of the bent body, wherein the at least one guiding path is formed proximal to a transverse edge of the bent body;

wherein the at least one guiding element is configured such that said at least one of the one or more guiding path comprises a first guiding path formed proximal to one transverse edge of the bent body and/or a second guiding path formed proximal to the other transverse edge of the bent body.

12. The implant system of claim 1, wherein the middle portion of the bent body is tilted at the closed end with respect to a transverse direction of each of the lateral arms extending between opposing transverse edges of the bent body, such that a separation distance between the middle portion and the open end increases along the middle portion in the transverse direction.

13. The implant system of claim 1, wherein the bent body is a one-piece body.

14. The implant system of claim 1, further comprising a tensioning device for closing and tensioning the at least one tensioning element for pulling the first and second implant devices towards each other.

15. The implant system of claim 1, wherein the bent body of each of the first implant device and the second implant device comprises one or more through-openings connecting an exterior surface of the corresponding bent body with an interior surface of the corresponding bent body;

wherein the implant system further comprises:

a first fixation element for fixating the first implant device to a ground material, in particular to a first bone or bone part by being received through one of the through-openings of the first implant device; and a second fixation element for fixating the second implant device to a ground material, in particular to a second bone or bone part, by being received through one of the through-openings of the second implant device;

wherein the first fixation element and/or the second fixation element comprises or is a fixation screw.

16. An implant system for re-joining a disjoined pubic symphysis comprising:

a first implant device and a second implant device, each of the first implant device and the second implant device comprising:

a bent body comprising a curved middle portion and two lateral arms, wherein the two lateral arms extend away from the middle portion and are mutually joined by the middle portion, such that the bent body defines an open end between the two lateral arms opposite a closed end defined by the middle portion; and at least one guiding element defining at least one guiding path extending along at least a portion of the bent body, wherein each of the at least one guiding path comprises a path vertex and two path portions extending away from the path vertex and from the closed end of the bent body;

each of the first implant device and the second implant device being configured for being fixated to a corresponding bone or bone part of a hemipelvis by form-fitting, such that the corresponding bone or bone part abuts against the interior surface of the respective bent body at its middle portion and such that each of the two lateral arms extend on one respective side of said bone or bone part;

at least one fixation cable configured for pulling the first and second implant devices towards each other by tension by being guided along one or more of the at least one guiding path of the first implant device and along one or more of the at least one guiding path of the second implant device, such that the first and second implant devices pull both hemipelvises together and cause the pubic symphysis to re-join; and a tensioning device for adjusting a pulling force acting upon the first and second implant devices by regulating a length of a tensioned portion of the at least one fixation cable.

17. A method of fixating together a first bone or bone part and a second bone or bone part for re-joining a disjoined pubic symphysis, using an implant system comprising:

a first implant device and a second implant device, each of the first implant device and the second implant device being configured for being fixated to a corresponding hemipelvis by form-fitting;

wherein each of the first implant device and the second implant device comprises:

a bent body comprising a curved middle portion and two lateral arms, wherein the two lateral arms extend away from the middle portion and are mutually joined by the middle portion, such that the bent body defines an open end between the two lateral arms opposite a closed end defined by the middle portion; and at least one guiding element defining at least one guiding path extending along at least a portion of the bent body, wherein each of the at least one guiding path comprises a path vertex and two path portions extending away from the path vertex and from the closed end of the bent body; and at least one tensioning element configured for pulling the first and second implant devices towards each other by tension by being guided along one or more of the at least one guiding path of the first implant device and along one or more of the at least one guiding path of the second implant device, such that the first and second implant devices pull both hemipelvises together and cause the pubic symphysis to re-join;

the method comprising:

arranging the first implant device around the first bone or bone part of a first hemipelvis, such that the first bone or bone part is partly surrounded by the bent body of the first implant device;

arranging the second implant device around the second bone or bone part of a second hemipelvis, such that the second bone or bone part is partly surrounded by the bent body of the second implant device; and pulling the first and second implant devices towards each other by tensioning the at least one tensioning element, thereby pulling both hemipelvises together and causing the pubic symphysis to re-join, wherein the at least one tensioning element is arranged along one or more of the at least one guiding path of the first implant device and along one or more of the at least one guiding path of the second implant device.

18. The method of claim 17, wherein arranging the first implant device around the first bone or bone part comprises fixating the first implant device to the first bone or bone part, using a first fixation element passing through at least one of one or more through-openings formed in the bent body of the first implant device; and/or wherein arranging the second implant device around the second bone or bone part comprises fixating the second implant device to the second bone or bone part, and using a second fixation element passing through at least one of one or more through-openings formed in the bent body of the second implant device.

19. The method of claim 17, wherein the at least one tensioning element extends between one lateral arm of the first implant device and one lateral arm of the second implant device on one side of the first bone or bone part and on the same side of the second bone or bone part.

20. The method of claim 17, wherein the at least one tensioning element extends between one lateral arm of the first implant device and one lateral arm of the second implant device and between the other lateral arm of the first implant device and the other lateral arm of the second implant device on two sides of the first bone or bone part and on the same two sides of the second bone or bone part.

* * * * *